с11207516B2

United States Patent
Bluvshtein et al.

(10) Patent No.: US 11,207,516 B2
(45) Date of Patent: Dec. 28, 2021

(54) DISTRIBUTED TRANSFORMER

(71) Applicant: Minnetronix, Inc., St. Paul, MN (US)

(72) Inventors: Vlad Bluvshtein, Plymouth, MN (US); Lori Lucke, Rosemount, MN (US)

(73) Assignee: Minnetronix, Inc., St. Paul, MN (US)

( * ) Notice: Subject to any disclaimer, the term of this patent is extended or adjusted under 35 U.S.C. 154(b) by 112 days.

(21) Appl. No.: 16/505,176

(22) Filed: Jul. 8, 2019

(65) Prior Publication Data

US 2019/0328949 A1    Oct. 31, 2019

Related U.S. Application Data

(62) Division of application No. 14/994,625, filed on Jan. 13, 2016, now Pat. No. 10,342,908.

(Continued)

(51) Int. Cl.
| | |
|---|---|
| *A61M 60/871* | (2021.01) |
| *A61N 1/378* | (2006.01) |
| *H02J 7/02* | (2016.01) |
| *H02J 50/50* | (2016.01) |
| *A61M 60/40* | (2021.01) |
| *A61M 60/122* | (2021.01) |

(Continued)

(52) U.S. Cl.
CPC ......... *A61M 60/871* (2021.01); *A61N 1/3787* (2013.01); *A61M 60/122* (2021.01); *A61M 60/148* (2021.01); *A61M 60/205* (2021.01); *A61M 60/274* (2021.01); *A61M 60/40* (2021.01); *A61M 2205/04* (2013.01); *A61M 2205/8237* (2013.01); *A61M 2205/8243* (2013.01); *H02J 7/025* (2013.01); *H02J 50/50* (2016.02)

(58) Field of Classification Search
CPC ........ A61M 60/873; A61M 2205/8243; A61N 1/3878; A61N 1/37223; A61N 1/37229
See application file for complete search history.

(56) References Cited

U.S. PATENT DOCUMENTS

| | | |
|---|---|---|
| 3,195,540 A | 7/1965 | Waller |
| 3,566,876 A | 3/1971 | Stoft et al. |

(Continued)

FOREIGN PATENT DOCUMENTS

| | | |
|---|---|---|
| DE | 102006037668 A1 | 3/2007 |
| DE | 102015112097 A1 | 1/2016 |

(Continued)

OTHER PUBLICATIONS

Ng et al, "Wireless Power Delivery for Retinal Prostheses", 33rd Annual internation Conference of the IEEE EMBS, Boston Mass, Aug. 20-Sep. 3, 2011. (Year: 2011).*

(Continued)

*Primary Examiner* — George R Evanisko
(74) *Attorney, Agent, or Firm* — Seager, Tufte & Wickhem, LLP

(57) ABSTRACT

Disclosed is a distributed transformer or extension cord component for a transcutaneous energy transfer system used to transfer electric power to an implanted medical device. The extension cord component may enable power transfer to occur at various points on or near the body of the subject within whom the medical device is implanted. In this way, the subject may gain greater flexibility and high levels of convenience in connection with use of the transcutaneous energy transfer system.

13 Claims, 19 Drawing Sheets

Related U.S. Application Data

(60) Provisional application No. 62/103,258, filed on Jan. 14, 2015.

(51) Int. Cl.
   *A61M 60/148* (2021.01)
   *A61M 60/205* (2021.01)
   *A61M 60/274* (2021.01)

(56) References Cited

U.S. PATENT DOCUMENTS

| | | |
|---|---|---|
| 3,756,246 A | 9/1973 | Thaler et al. |
| 3,760,332 A | 9/1973 | Berkovits et al. |
| 3,806,807 A | 4/1974 | Nakamura |
| 3,943,535 A | 3/1976 | Schulman |
| 4,082,097 A | 4/1978 | Mann et al. |
| 4,143,661 A | 3/1979 | LaForge et al. |
| 4,164,946 A | 8/1979 | Langer |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Simmons et al. |
| 4,361,153 A | 11/1982 | Slocum et al. |
| 4,417,349 A | 11/1983 | Hills et al. |
| 4,439,806 A | 3/1984 | Brajder |
| 4,441,210 A | 4/1984 | Hochmair et al. |
| 4,446,513 A | 5/1984 | Clenet |
| 4,453,537 A | 6/1984 | Spitzer |
| 4,469,104 A | 9/1984 | Peers-Trevarton |
| 4,494,545 A | 1/1985 | Slocum et al. |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,681,111 A | 7/1987 | Silvian |
| 4,691,270 A | 9/1987 | Pruitt |
| 4,706,689 A | 11/1987 | Man |
| 4,768,512 A | 9/1988 | Imran |
| 4,774,950 A | 10/1988 | Cohen |
| 4,848,346 A | 7/1989 | Crawford |
| 4,855,888 A | 8/1989 | Henze et al. |
| 4,898,173 A | 2/1990 | Daglow et al. |
| 4,924,171 A | 5/1990 | Baba et al. |
| 4,925,443 A | 5/1990 | Heilman et al. |
| 4,933,798 A | 6/1990 | Widmayer et al. |
| 4,941,652 A | 6/1990 | Nagano et al. |
| 4,941,201 A | 7/1990 | Davis |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,012,807 A | 5/1991 | Stutz, Jr. |
| 5,076,270 A | 12/1991 | Stutz, Jr. |
| 5,132,888 A | 7/1992 | Lo et al. |
| 5,132,889 A | 7/1992 | Hitchcock et al. |
| 5,157,593 A | 10/1992 | Jain |
| 5,158,097 A | 10/1992 | Christlieb |
| 5,205,810 A | 4/1993 | Guiraudon et al. |
| 5,279,292 A | 1/1994 | Baumann et al. |
| 5,314,457 A | 5/1994 | Jeutter et al. |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,413,595 A | 5/1995 | Stutz, Jr. |
| 5,438,498 A | 8/1995 | Ingemi |
| 5,444,608 A | 8/1995 | Jain |
| 5,456,715 A | 10/1995 | Liotta |
| 5,499,178 A | 3/1996 | Mohan |
| 5,500,004 A | 3/1996 | Ansourian et al. |
| 5,515,264 A | 5/1996 | Stacey |
| 5,522,865 A | 6/1996 | Schuman et al. |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,662,692 A | 9/1997 | Paspa et al. |
| 5,674,281 A | 10/1997 | Snyder |
| 5,690,693 A | 11/1997 | Wang et al. |
| 5,702,427 A | 12/1997 | Ecker et al. |
| 5,702,431 A | 12/1997 | Wang et al. |
| 5,704,891 A | 1/1998 | Mussivand |
| 5,713,939 A | 2/1998 | Nedungadi et al. |
| 5,713,954 A | 2/1998 | Rosenberg et al. |
| 5,722,930 A | 3/1998 | Larson, Jr. et al. |
| 5,728,154 A | 3/1998 | Crossett et al. |
| 5,735,887 A | 4/1998 | Barreras, Sr. et al. |
| 5,741,314 A | 4/1998 | Daly et al. |
| 5,741,316 A | 4/1998 | Chen et al. |
| 5,749,909 A | 5/1998 | Schroeppel et al. |
| 5,751,125 A | 5/1998 | Weiss |
| 5,755,748 A | 5/1998 | Borza |
| 5,781,419 A | 7/1998 | Kutkut et al. |
| 5,945,762 A | 8/1999 | Chen et al. |
| 5,948,006 A | 9/1999 | Mann |
| 5,991,665 A | 11/1999 | Wang et al. |
| 5,995,874 A | 11/1999 | Borza |
| 6,047,214 A | 4/2000 | Mueller et al. |
| 6,058,330 A | 5/2000 | Borza |
| 6,067,474 A | 5/2000 | Schulman et al. |
| 6,076,016 A | 6/2000 | Feierbach |
| 6,088,619 A | 7/2000 | Hein et al. |
| 6,092,531 A | 7/2000 | Chen et al. |
| 6,112,121 A | 8/2000 | Paul et al. |
| 6,149,683 A | 11/2000 | Lancisi et al. |
| 6,212,430 B1 | 4/2001 | Kung |
| 6,233,485 B1 | 5/2001 | Armstrong et al. |
| 6,240,318 B1 | 5/2001 | Phillips |
| 6,254,525 B1 | 7/2001 | Reinhardt et al. |
| 6,263,247 B1 | 7/2001 | Mueller et al. |
| 6,275,737 B1 | 8/2001 | Mann |
| 6,324,430 B1 | 11/2001 | Zarinetchi et al. |
| 6,342,071 B1 | 1/2002 | Pless |
| 6,345,203 B1 | 2/2002 | Mueller et al. |
| 6,366,817 B1 | 4/2002 | Kung |
| 6,389,318 B1 | 5/2002 | Zarinetchi et al. |
| 6,400,991 B1 | 6/2002 | Kung |
| 6,424,867 B1 | 7/2002 | Snell |
| 6,430,444 B1 | 8/2002 | Borza |
| 6,434,194 B1 | 8/2002 | Eisenberg et al. |
| 6,442,434 B1 | 8/2002 | Zarinetchi et al. |
| 6,443,891 B1 | 9/2002 | Grevious |
| 6,451,055 B1 | 9/2002 | Weiss |
| 6,458,164 B1 | 10/2002 | Weiss |
| 6,478,820 B1 | 11/2002 | Weiss |
| 6,517,476 B1 | 2/2003 | Bedoya et al. |
| 6,579,315 B1 | 6/2003 | Weiss |
| 6,592,620 B1 | 7/2003 | Lancisi et al. |
| 6,641,612 B2 | 11/2003 | Pless |
| 6,648,914 B2 | 11/2003 | Berrang et al. |
| 6,671,554 B2 | 12/2003 | Gibson et al. |
| 6,810,289 B1 | 10/2004 | Shaquer |
| 6,831,944 B1 | 12/2004 | Misra et al. |
| 6,850,803 B1 | 2/2005 | Jimenez |
| 6,862,478 B1 | 3/2005 | Goldstein |
| 6,961,005 B2 | 11/2005 | Clement et al. |
| 6,978,181 B1 | 12/2005 | Snell |
| 7,003,353 B1 | 2/2006 | Parkhouse |
| 7,035,689 B1 | 4/2006 | Hawkins et al. |
| 7,062,331 B2 | 6/2006 | Zarinetchi et al. |
| 7,069,086 B2 | 6/2006 | Von Arx |
| 7,076,206 B2 | 7/2006 | Elferich et al. |
| 7,079,901 B1 | 7/2006 | Loftin et al. |
| 7,155,291 B2 | 12/2006 | Zarinetchi et al. |
| 7,173,411 B1 | 2/2007 | Pond |
| 7,191,007 B2 | 3/2007 | Desai et al. |
| 7,299,095 B1 | 11/2007 | Barlow et al. |
| 7,317,947 B2 | 1/2008 | Wahlstrand et al. |
| 7,512,443 B2 | 3/2009 | Phillips et al. |
| 7,515,967 B2 | 4/2009 | Phillips |
| 7,574,262 B2 | 8/2009 | Haugland et al. |
| 7,599,743 B2 | 10/2009 | Hassler, Jr. et al. |

(56) References Cited

U.S. PATENT DOCUMENTS

| | | | |
|---|---|---|---|
| 7,672,732 B2 | 3/2010 | Sun et al. |
| 7,738,965 B2 | 6/2010 | Phillips et al. |
| 7,774,069 B2 | 8/2010 | Olson |
| 7,781,916 B2 | 8/2010 | Boys |
| 7,822,480 B2 | 10/2010 | Park et al. |
| 7,848,814 B2 | 12/2010 | Torgerson et al. |
| 7,962,211 B2 | 6/2011 | Torgerson et al. |
| 8,024,047 B2 | 9/2011 | Olson et al. |
| 8,027,735 B1 | 9/2011 | Tziviskos et al. |
| 8,032,486 B2 | 10/2011 | Townsend et al. |
| 8,050,068 B2 | 11/2011 | Hussmann et al. |
| 8,093,758 B2 | 1/2012 | Hussmann |
| 8,097,983 B2 | 1/2012 | Karalis et al. |
| 8,116,681 B2 | 2/2012 | Baarman |
| 8,126,563 B2 | 2/2012 | Ibrahim |
| 8,265,770 B2 | 9/2012 | Toy et al. |
| 8,311,638 B2 | 11/2012 | Aghassian |
| 8,428,712 B2 | 4/2013 | Davis et al. |
| 8,428,724 B2 | 4/2013 | Sage |
| 8,437,855 B2 | 5/2013 | Sjostedt et al. |
| 8,457,758 B2 | 6/2013 | Olson |
| 8,473,066 B2 | 6/2013 | Aghassian et al. |
| 8,515,112 B2 | 8/2013 | Crawford et al. |
| 8,543,209 B2 | 9/2013 | Tyers et al. |
| 8,626,308 B2 | 1/2014 | Meskens |
| 8,630,717 B2 | 1/2014 | Olson et al. |
| 8,676,337 B2 | 3/2014 | Kallmyer |
| 8,706,255 B2 | 4/2014 | Philips et al. |
| 8,738,148 B2 | 5/2014 | Olson et al. |
| 8,764,621 B2 | 6/2014 | Badstibner et al. |
| 8,766,788 B2 | 7/2014 | D'Ambrosio |
| 8,903,515 B2 | 12/2014 | Mashiach |
| 8,972,012 B2 | 3/2015 | Lim |
| 9,192,772 B1 | 11/2015 | Kishiyama et al. |
| 9,603,984 B2 | 3/2017 | Romero et al. |
| 9,855,376 B2 | 1/2018 | Bluvshtein et al. |
| 10,149,933 B2 | 12/2018 | Bluvshtein et al. |
| 10,193,395 B2 | 1/2019 | Bluvshtein et al. |
| 10,376,625 B2 | 8/2019 | Bluvshtein et al. |
| 10,406,267 B2 | 9/2019 | Lucke et al. |
| 2002/0021226 A1 | 2/2002 | Clement et al. |
| 2002/0032471 A1 | 3/2002 | Loftin et al. |
| 2002/0087204 A1 | 7/2002 | Kung et al. |
| 2002/0128709 A1 | 9/2002 | Pless |
| 2002/0177884 A1 | 11/2002 | Ahn et al. |
| 2003/0045912 A1 | 3/2003 | Williams et al. |
| 2003/0085684 A1 | 5/2003 | Tsukamoto et al. |
| 2003/0171792 A1 | 9/2003 | Zarinetchi et al. |
| 2004/0034393 A1 | 2/2004 | Hansen et al. |
| 2004/0039423 A1 | 2/2004 | Dolgin |
| 2004/0049245 A1 | 3/2004 | Gass et al. |
| 2005/0065570 A1 | 3/2005 | Stein et al. |
| 2005/0075694 A1 | 4/2005 | Schmeling et al. |
| 2005/0075696 A1 | 4/2005 | Forsberg et al. |
| 2005/0131491 A1 | 6/2005 | Shaquer |
| 2005/0222624 A1* | 10/2005 | Greenberg ......... A61N 1/36046 607/2 |
| 2005/0245996 A1 | 11/2005 | Phillips et al. |
| 2005/0288739 A1 | 12/2005 | Hassler, Jr. et al. |
| 2005/0288741 A1 | 12/2005 | Hassler, Jr. et al. |
| 2006/0020305 A1 | 1/2006 | Desai et al. |
| 2006/0036127 A1 | 2/2006 | Delgado, III |
| 2006/0167333 A1 | 7/2006 | Moore et al. |
| 2006/0184204 A1 | 8/2006 | He |
| 2006/0247737 A1 | 11/2006 | Olson |
| 2006/0267790 A1 | 11/2006 | Matthiessen et al. |
| 2007/0060787 A1 | 3/2007 | Peters et al. |
| 2007/0255349 A1 | 11/2007 | Torgerson et al. |
| 2007/0255350 A1 | 11/2007 | Torgerson et al. |
| 2008/0065173 A1 | 3/2008 | Wahlstrand et al. |
| 2008/0198947 A1 | 8/2008 | Zierhofer |
| 2008/0255631 A1 | 10/2008 | Sjostedt et al. |
| 2008/0303480 A1 | 12/2008 | Prutchi et al. |
| 2009/0067653 A1 | 3/2009 | Meskens et al. |
| 2009/0281597 A1 | 11/2009 | Parramon et al. |
| 2010/0010582 A1 | 1/2010 | Carbunaru et al. |
| 2010/0033023 A1 | 2/2010 | Baarman |
| 2010/0033240 A1 | 2/2010 | Denison et al. |
| 2010/0063347 A1 | 3/2010 | Yomtov et al. |
| 2010/0164296 A1 | 7/2010 | Kurs et al. |
| 2010/0249886 A1 | 9/2010 | Park et al. |
| 2010/0268305 A1 | 10/2010 | Olson |
| 2010/0292759 A1 | 11/2010 | Hahn |
| 2010/0327887 A1 | 12/2010 | Denison et al. |
| 2011/0004278 A1 | 1/2011 | Aghassian et al. |
| 2011/0093048 A1 | 4/2011 | Aghassian |
| 2011/0101790 A1 | 5/2011 | Budgett |
| 2011/0106210 A1 | 5/2011 | Meskens |
| 2011/0301669 A1 | 12/2011 | Olson |
| 2011/0313490 A1 | 12/2011 | Parramon et al. |
| 2012/0032522 A1 | 2/2012 | Schatz et al. |
| 2012/0095528 A1 | 4/2012 | Miller, III et al. |
| 2012/0154143 A1 | 6/2012 | D'Ambrosio |
| 2012/0157753 A1 | 6/2012 | D'Ambrosio |
| 2012/0157754 A1 | 6/2012 | D'Ambrosio |
| 2012/0197352 A1 | 8/2012 | Carbunaru et al. |
| 2012/0215285 A1 | 8/2012 | Tahmasian |
| 2012/0265003 A1 | 10/2012 | D'Ambrosio et al. |
| 2013/0023958 A1 | 1/2013 | Fell |
| 2013/0041429 A1 | 2/2013 | Aghassian |
| 2013/0043736 A1 | 2/2013 | Zilbershlag |
| 2013/0046361 A1 | 2/2013 | DiGiore et al. |
| 2013/0123881 A1 | 5/2013 | Aghassian |
| 2013/0127253 A1 | 5/2013 | Stark |
| 2013/0158631 A1 | 6/2013 | Shea et al. |
| 2013/0163688 A1 | 6/2013 | Calvin |
| 2013/0278226 A1 | 10/2013 | Cong et al. |
| 2013/0310629 A1 | 11/2013 | Lafontaine |
| 2013/0317345 A1 | 11/2013 | Frustaci et al. |
| 2013/0331638 A1 | 12/2013 | Cameron et al. |
| 2013/0338734 A1 | 12/2013 | Hoyer et al. |
| 2014/0005749 A1 | 1/2014 | Stahmann et al. |
| 2014/0031607 A1 | 1/2014 | Zilbershlag et al. |
| 2014/0139034 A1 | 5/2014 | Sankar et al. |
| 2014/0243944 A1 | 8/2014 | Stevenson et al. |
| 2014/0371823 A1 | 12/2014 | Mashiach et al. |
| 2015/0069847 A1 | 3/2015 | Meyer et al. |
| 2015/0073203 A1 | 3/2015 | Wariar et al. |
| 2015/0207331 A1 | 7/2015 | Petersen |
| 2015/0209591 A1 | 7/2015 | Meskens |
| 2015/0333801 A1 | 11/2015 | Hosotani |
| 2015/0364861 A1 | 12/2015 | Lucke et al. |
| 2015/0380988 A1 | 12/2015 | Chappell et al. |
| 2016/0175600 A1 | 6/2016 | Amir et al. |
| 2016/0197511 A1 | 7/2016 | Atasoy et al. |
| 2016/0206799 A1 | 7/2016 | Lucke et al. |
| 2016/0248265 A1 | 8/2016 | Oo et al. |
| 2016/0294225 A1 | 10/2016 | Blum et al. |
| 2016/0303301 A1 | 10/2016 | Bluvshtein et al. |
| 2017/0119947 A1 | 5/2017 | Eldridge et al. |
| 2018/0207338 A1 | 7/2018 | Bluvshtein et al. |
| 2019/0111198 A1 | 4/2019 | Bluvshtein et al. |
| 2019/0157913 A1 | 5/2019 | Bluvshtein et al. |

FOREIGN PATENT DOCUMENTS

| | | |
|---|---|---|
| FR | 2587221 | 3/1987 |
| JP | 2597623 B2 | 4/1997 |
| WO | 8301006 | 3/1983 |
| WO | 8700420 | 1/1987 |
| WO | 9809588 | 3/1998 |
| WO | 0191678 A1 | 12/2001 |
| WO | 2007126454 A2 | 11/2007 |
| WO | 2008106717 A1 | 9/2008 |
| WO | 2009029977 A1 | 3/2009 |
| WO | 2010042057 A1 | 4/2010 |
| WO | 2010133702 A2 | 11/2010 |
| WO | 2011119352 A1 | 9/2011 |
| WO | 2012077088 A2 | 6/2012 |
| WO | 2012077088 A3 | 6/2012 |

(56) References Cited

FOREIGN PATENT DOCUMENTS

WO      2014036449 A1    3/2014
WO      2014169940 A1    10/2014

OTHER PUBLICATIONS

"Modulator (in German, with translation)", Wikipedia Version 20130328.

Andia, et al., "Closed Loop Wireless Power Transmission for Implantable Medical Devices," IEEE, 2011, pp. 404-407.

Bonsor, "How Artificial Hearts Work," HowStuffWorks, Aug. 9, 2001, downloaded from HowStuffWorks.com. at http://science.howstuffworks.com/innovation/everyday-innovations/artificial-heart.htm (12 pages).

German Patent & Trademark Office, , "First Office Action", Application No. 102016106683.4, dated Mar. 5, 2018, 17 pages.

Knecht, et al., "Optimization of Transcutaneous Energy Transfer Coils for High Power Medical Applications," Workshop on Control and Modeling for Power Electronics (COMPEL), 2014, pp. 1-10.

Ng, et al., "Closed-Loop Inductive Link for Wireless Powering of a High Density Electrode Array Retinal Prosthesis," IEEE, 2009, pp. 92-97.

Ng, et al., "Wireless Power Delivery for Retinal Prostheses," 33rd Annual International Conference of the IEEE EMBS, Aug. 30, 2011-Sep. 3, 2011, pp. 8356-8360.

Shmilovitz, et al., "Noninvasive Control of the Power Transferred to an Implanted Device by an Ultrasonic Transcutaneous Energy Transfer Link," IEEE Transactions on Biomedical Engineering, Apr. 2014, pp. 995-1004, vol. 61, No. 4.

Mirbozorgi, et al., "A Transcutaneous Power Transfer Interface Based on a Multicoil Inductive Link", Aug. 28-Sep. 1, 2012, pp. 1659-1662, 34th Annual International Conference of the IEEE EMBS, San Diego, CA.

Ng, et al., "Wireless Power Delivery for Retinal Prostheses", 33rd Annual International Conference of the IEEE EMBS, pp. 8356-8360, Aug. 30-Sep. 3, 2011, Boston MA.

* cited by examiner

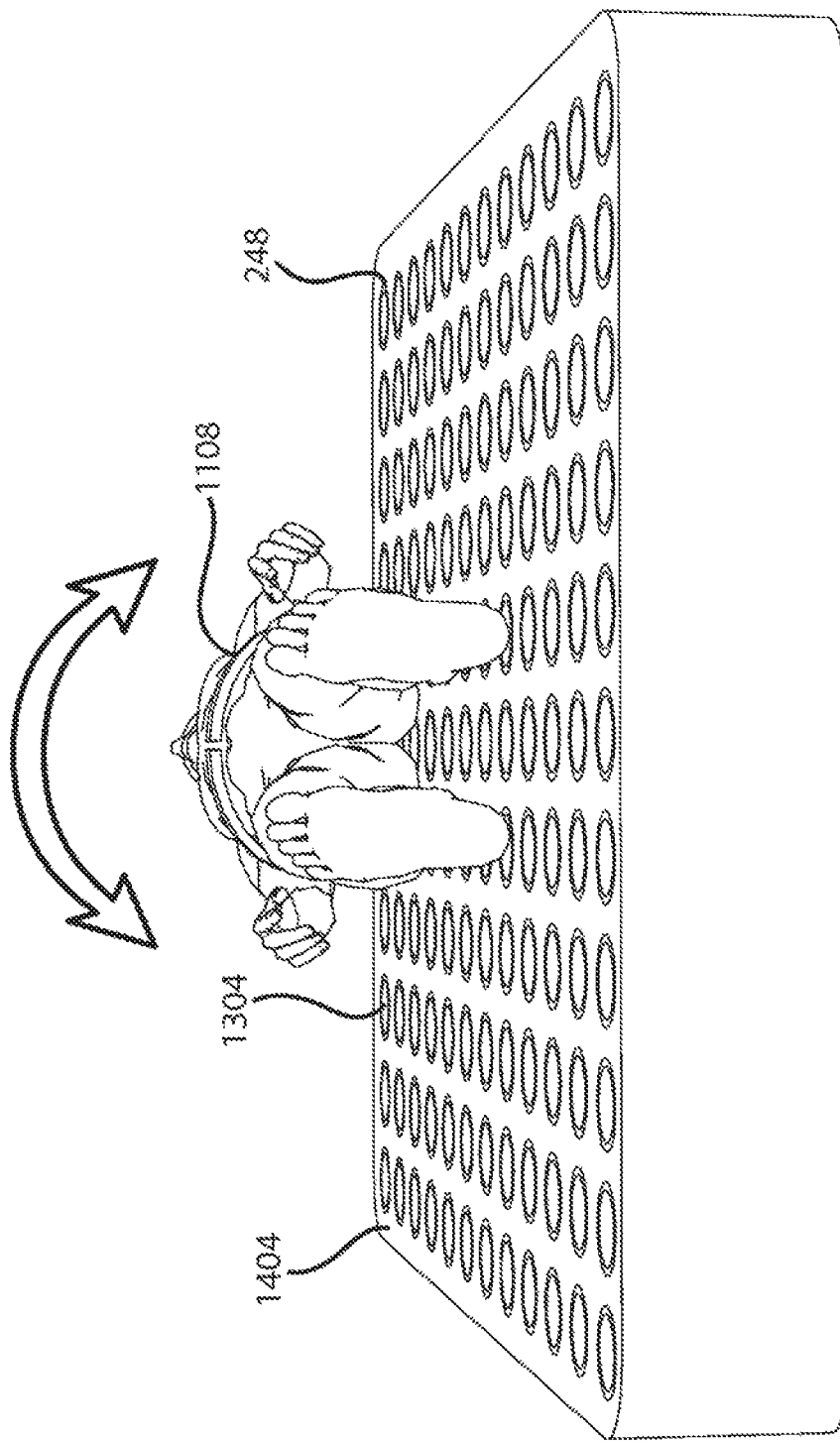

DISTRIBUTED TRANSFORMER

CROSS-REFERENCE TO RELATED APPLICATIONS

This application is a division of U.S. application Ser. No. 14/994,625, filed Jan. 13, 2016, now U.S. Pat. No. 10,342,908, which claims the benefit of U.S. Provisional Application No. 62/103,258, filed Jan. 14, 2015. The entirety of each are herein incorporated by reference.

TECHNICAL FIELD

The technology described herein relates to a distributed transformer or extension cord component for a transcutaneous energy transfer system.

BACKGROUND

Currently, there is a need to deliver electric power to implanted medical devices such as artificial hearts and ventricle assist devices. It is possible to deliver power non-invasively through electromagnetic energy transmitted through the skin. This technology can provide life sustaining benefits. However, those who use the technology may suffer reduced mobility or other inconveniences. For example, a subject within whom a medical device is implanted may be somewhat tethered to the electrical power cords and devices that provide the continuous power needed for some devices, such as ventricle assist devices. Thus, the ability of the subject to move about or to take part in certain activities such as swimming may be limited or nonexistent. Prior art systems fail to provide mechanisms for addressing these and other issues that concern the quality of life for those that use a system for transferring electromagnetic energy to implanted medical devices. These and other deficiencies of the prior art are addressed herein.

SUMMARY

Present embodiments are directed to a distributed transformer or extension cord component for a transcutaneous energy transfer system. The transcutaneous energy transfer system may operate to transfer electric power to an implanted medical device. The medical device may be implanted in a subject and can include an artificial heart or ventricle assist device. In one respect, the extension cord component enables power transfer to occur at various points on or near the body of the subject within whom the medical device is implanted. In this way, the subject may gain greater flexibility and high levels of convenience in connection with use of the transcutaneous energy transfer system.

In one aspect, a distributed transformer of a transcutaneous energy transmission device is disclosed, the distributed transformer component comprising a first transformer including a primary winding and a secondary winding, the primary winding associated with a power supply, the first transformer configured to transfer power from the primary winding to the secondary winding across a first boundary; a second transformer including a primary winding and a secondary winding, the secondary winding associated with a medical device implanted within a subject, the second transformer configured to transfer power from the primary winding to the secondary winding across a second boundary that includes at least the skin of the subject; and a cord that connects the secondary winding of the first transformer to the primary winding of the second transformer. In some implementations, the cord is removable.

In some implementations, the cord includes at least one capacitor connected between the secondary winding of the first transformer and the primary winding of the second transformer.

In some implementations, the first transformer is configured for any shape or size, any location, and any orientation or combination thereof; and the second transformer is configured for a fixed implant location within the subject.

In some implementations, the cord between the first transformer and the second transformer allows greater separation between the primary of the first transformer and the secondary of the second transformer In some implementations, the first transformer is configured for a higher VA rating, a larger or smaller coupling range between the windings or a higher temperature operation than the second transformer.

In some implementations, the first boundary includes an article of clothing worn by the subject.

In some implementations, the article of clothing is a vest.

In some implementations, the article of clothing is a backpack.

In some implementations, the article of clothing includes the power supply and the primary winding of the first transformer; and the secondary winding of the first transformer, the cord, and the primary winding of the second transformer are attached to the subject.

In some implementations, the article of clothing includes the power supply and the primary and secondary windings of the first transformer; and a portion of the cord and the primary winding of the second transformer are attached to subject.

In some implementations, the article of clothing includes the power supply, the first transformer, and the primary winding of the second transformer.

In some implementations, the article of clothing includes the secondary winding of the first transformer, the primary winding of the second transformer, and the cord; and the power supply and the primary winding of the first transformer are worn by the subject in a separate article of clothing.

In some implementations, the primary winding of the first transformer is a single coil; and the secondary winding of the first transformer is in an inductive track configured to wrap around the body of the subject; and the inductive track is at least one of a rectangular inductive loop or a plurality of sequentially connected coils.

In some implementations, the first boundary is a portion of an object used by the subject; and the power supply and the primary winding of the first transformer are embedded within the object.

In some implementations, the secondary winding of the transformer, the cord, and the primary winding of the second transformer are incorporated into an article of clothing configured to be worn by the subject; the secondary winding of the first transformer is positioned in the article of clothing so as to align with the primary winding of the first transformer the subject wears the article of clothing and uses the object; the first boundary includes a first portion of the article of clothing; and the second boundary includes a second portion of the article of clothing.

In some implementations, the article of clothing is a vest worn by the subject.

In some implementations, the object used by the subject is a piece of furniture and the primary winding of the first transformer is positioned in the piece of furniture so as to align with the secondary winding of the first transformer when the subject uses the piece of furniture.

In some implementations, the object used by the subject is a backpack and the primary winding of the first transformer is positioned in the backpack so as to align with the secondary winding of the first transformer when subject wears the backpack.

In some implementations, the backpack is waterproof.

In some implementations, the primary winding of the first transformer includes an array of coils arranged in a plane and embedded within the object used by the subject; the secondary winding of the first transformer is in an inductive track configured to wrap around the body of the subject; the inductive track is at least one of a rectangular inductive loop or a plurality of sequentially connected coils; and at least a portion of the secondary winding of the first transformer couples to the array of coils through at least one coil in the array of coils.

In some implementations, the amount of coupling between the secondary winding of the first transformer and the array of coils is unaffected by the rotational position of the subject about a longitudinal axis.

In some implementations, the secondary winding of the first transformer includes a plurality of coils arranged along a surface of the material.

In some implementations, the secondary winding of the first transformer includes a single inductive track arranged along a surface of the material.

In some implementations, the object used by the subject is a mattress.

In some implementations, the object used by the subject is a chair.

In another aspect, a method for transferring power across multiple boundaries in a transcutaneous energy transmission device is disclosed, the method comprising driving a primary winding of a first transformer with an electrical signal; inducing an electrical signal in a secondary winding of the first transformer by coupling at least a portion of the electrical signal in the primary winding of the first transformer across a first boundary; driving a primary winding of a second transformer with the electrical signal induced in the secondary winding of the first transformer, wherein the electrical signal is transmitted along a cord from the secondary winding of the first transformer to the primary winding of the second transformer; and inducing an electrical signal in a secondary winding of the second transformer implanted in a subject by coupling at least a portion of the electrical signal in the primary winding of the second transformer across a second boundary that includes the skin of the subject.

Some implementations include moving the secondary winding of the first transformer so as to translate a power transfer location on the body of the subject from a fixed location adjacent the implanted secondary winding of the second transformer to a variable location that is selectable by the subject.

In another respect, a distributed transformer of a transcutaneous energy transmission device is disclosed, the distributed transformer component comprising a first transformer including a primary winding and a secondary winding, the primary winding associated with a power supply, the first transformer configured to transfer power from the primary winding to the secondary winding across a first boundary that includes at least the skin of the subject; a second transformer including a primary winding and a secondary winding, the secondary winding associated with a medical device implanted within a subject, the second transformer configured to transfer power from the primary winding to the secondary winding across a second boundary; and a cord that connects the secondary winding of the first transformer to the primary winding of the second transformer.

In some implementations, the medical device is a mechanical circulatory device.

In some implementations, the cord includes at least one capacitor connected between the secondary winding of the first transformer and the primary winding of the second transformer.

In some implementations, the first transformer is configured for a fixed implant location within the subject; and the second transformer is configured for any shape or size, any location, and any orientation or combination thereof.

In some implementations, the second boundary includes a portion of an implanted medical device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIGS. 14A-B are illustrations of the distributed transformer embodiments of FIGS. 11A-B used in connection with an array of coils that is included within a mattress.

DETAILED DESCRIPTION

Present embodiments are directed to a distributed transformer or extension cord component for a transcutaneous energy transfer system. The transcutaneous energy transfer system may operate to transfer electric power to an implanted medical device. The medical device may be implanted in a subject and can include an artificial heart or ventricle assist device. In one respect, the extension cord component enables power transfer to occur at various points on or near the body of the subject within whom the medical device is implanted. In this way, the subject may gain greater flexibility and high levels of convenience in connection with use of the transcutaneous energy transfer system.

System Overview

Figure 1:
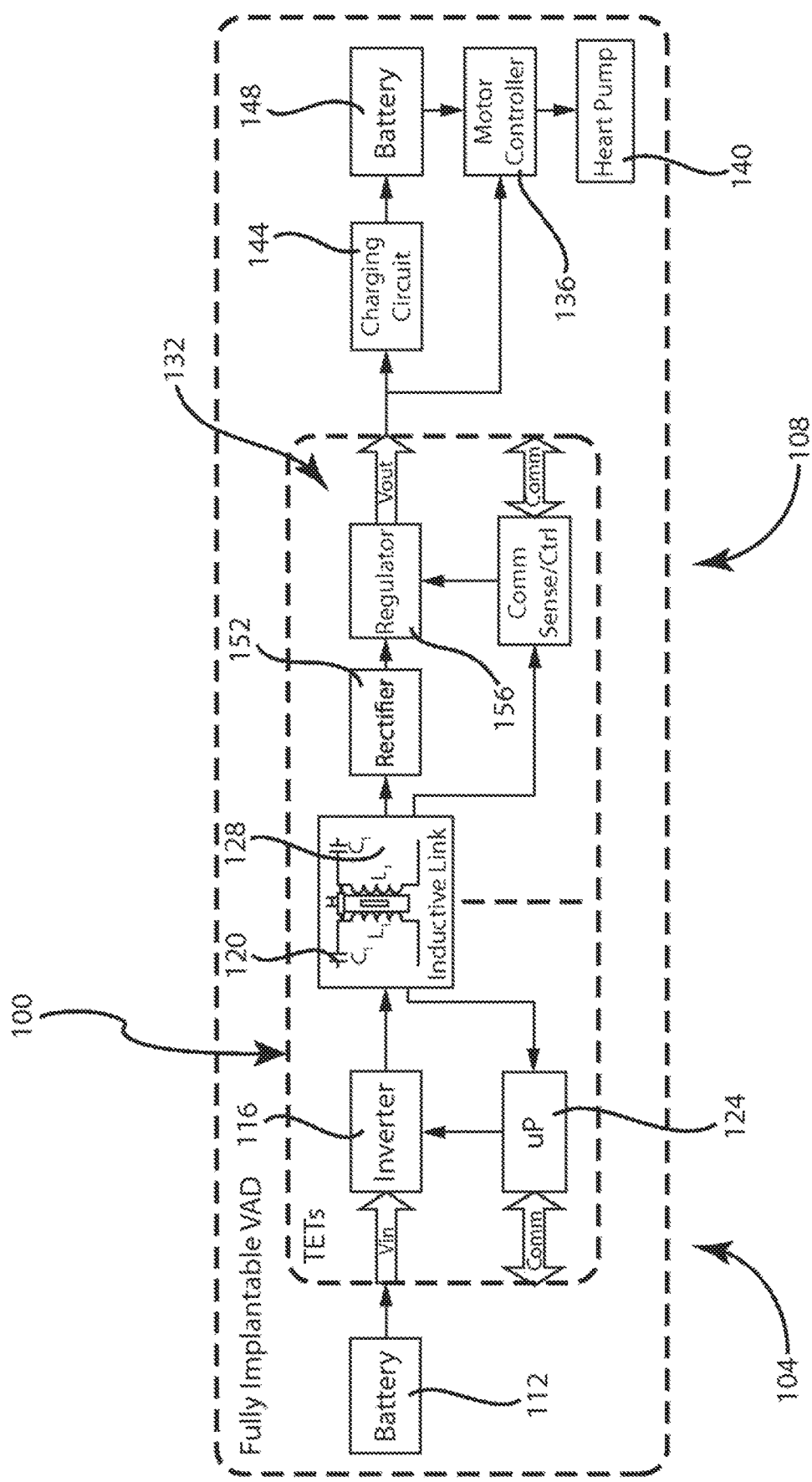
FIG. 1 is a block diagram of a wireless power transfer system in accordance with embodiments discussed herein.

FIG. 1 is a block diagram of a wireless power transfer system 100 in accordance with embodiments discussed herein. The system 100 may be referred to as a transcutaneous energy transfer system (TETS) when applied to implantable electronic applications. The system 100 has an external assembly 104 that is provided at an external location outside of a subject and an internal assembly 108 that is implanted within the subject. The internal assembly includes an implantable medical device. The implantable medical device may be any medical device capable of being implanted in a subject, such as a heart pump, an artificial heart, a right ventricle assist device, a left ventricle assist device, a BIVAD, a minimally invasive circulatory support system, a cardiac pace maker, and so on. While the implanted device may be any implantable medical device, this disclosure describes the transcutaneous energy transfer system 100 in the context of a heart pump 140 by way of example and not limitation.

Figure 2A:
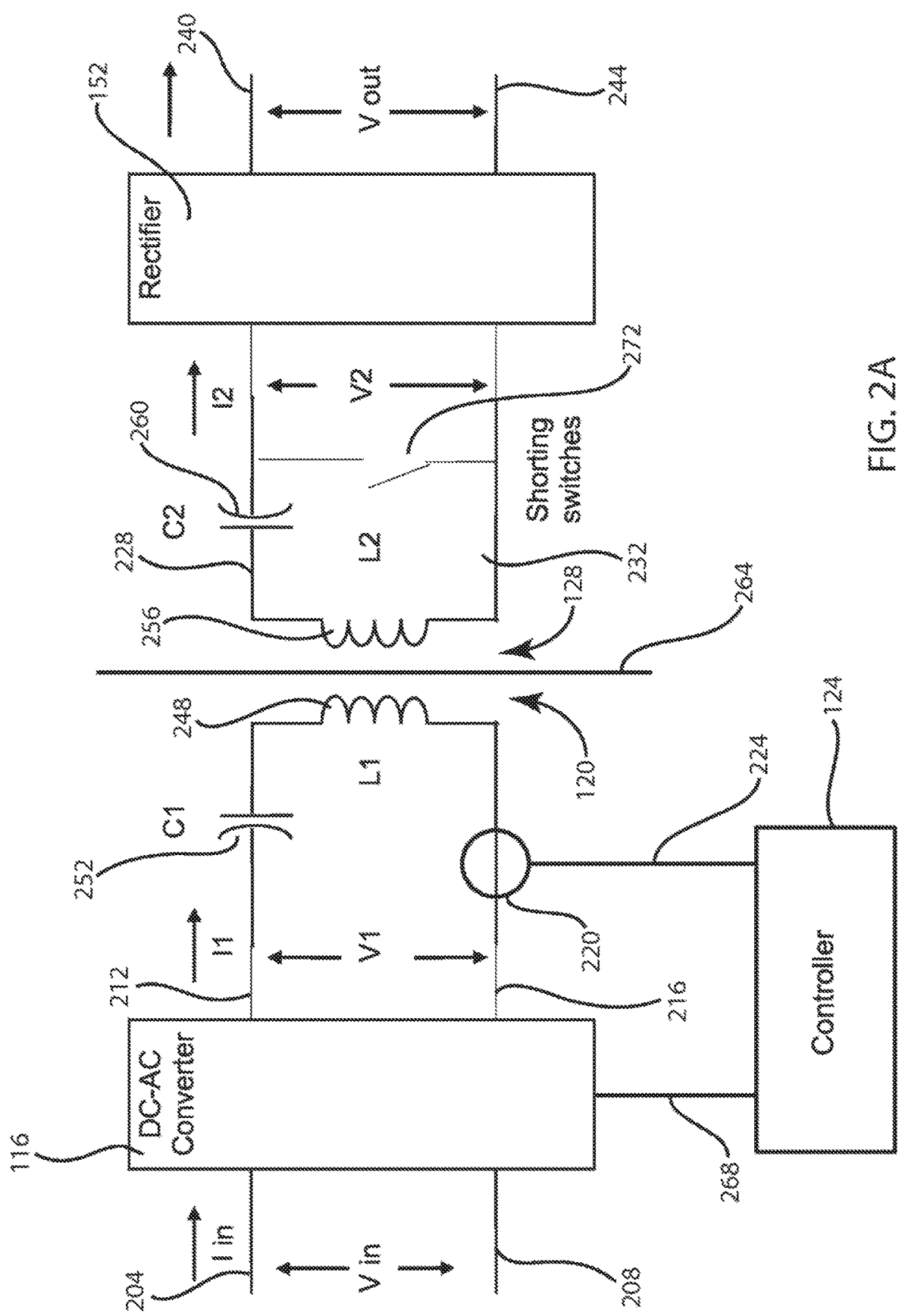
FIG. 2A is a circuit diagram for certain components of the system shown in FIG. 1.
Figure 2B:
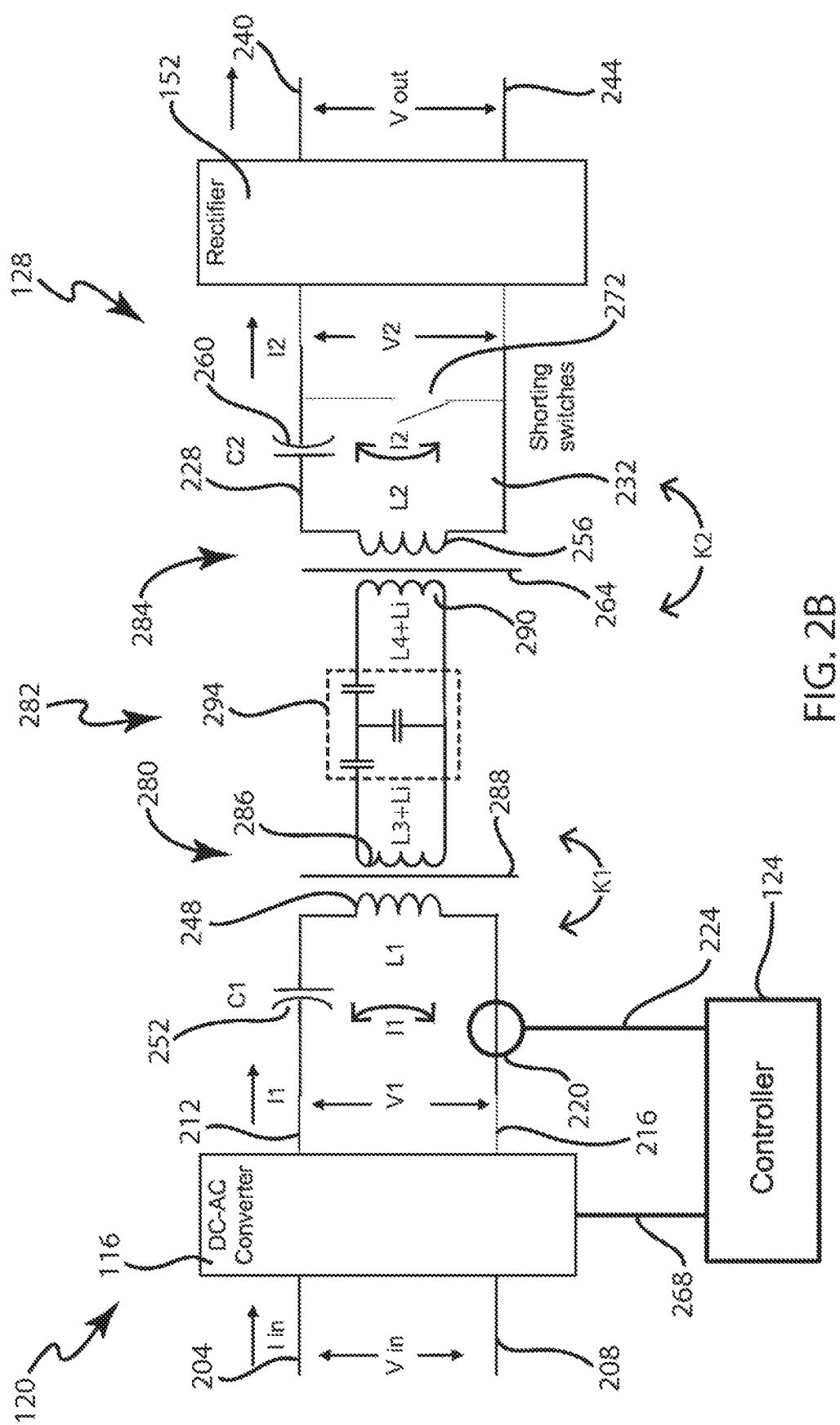
FIG. 2B is circuit diagram for certain components of the system shown in FIG. 1 that includes a distributed transformer.

As shown in FIG. 1, the external assembly 104 may include an external resonant network 120. Similarly, the internal assembly 108 may include an internal resonant network 128. The external assembly 104 and the internal assembly 108 are also shown in FIGS. 2A-B, which are circuit diagrams that include certain components of the transcutaneous energy transfer system 100. Embodiments of the transcutaneous energy transfer system 100 include a "distributed transformer" configuration where certain components are spatially separated from each other and interconnected or otherwise coupled to each other through an elongated component such as a cord or other assembly extension. In some implementations, the distributed transformer is associated with the external resonant network 120. In other implementations, the distributed transformer is associated with the internal resonant network 128. The circuit diagram of FIG. 2A illustrates the transcutaneous energy transfer system 100 without a distributed transformer in place; whereas, the circuit diagram of FIG. 2B illustrates the transcutaneous energy transfer system 100 with a distributed transformer 282 in place.

As shown in at least FIG. 2A, the external resonant network 120 may include an external coupler in the form of an inductive coil 248 and a capacitor 252 connected in series. Similarly, the internal resonant network 128 may include an internal coupler in the form of an inductive coil 256 and a capacitor 260 connected in series. The external resonant 120 may be configured such that the inductive coil 248 is connected directly to the inverter 116 through the capacitor 252. It should be appreciated that the series-series topology illustrated in at least FIG. 2A is shown by way of example and not limitation. Alternative embodiments may be used that employ different circuit topologies, such as series-parallel, parallel-series, parallel-parallel and so on.

FIG. 2B is a circuit diagram of an embodiment of the transcutaneous energy transfer system 100 that includes a distributed transformer 282 in accordance with the present disclosure. Like the embodiment shown in FIG. 2A, the internal resonant network 128 of FIG. 2B includes a coil 256 and a capacitor 260. Similarly, the external resonant network 120 includes an inductive coil 248 and a capacitor 252. In addition to these components, the external resonant network 120 of FIG. 2B includes first and second "extension cord" inductive coils 286, 290 and an "extension cord" capacitor or capacitor network 294. These components are referred to herein as "extension cord" components because, as described in greater detail below, these components may be embodied in a separate cord or other attachment. In one embodiment, the distributed transformer formed by the cord or other attachment couples to the remainder of the external resonant network 120 to thereby extend the distance between the coil 248 of the external resonant network 120 and the coil 256 of the internal resonant network 128. In other embodiments, the distributed transformer formed by the cord or other attachment may couple to the remainder of the internal network 128 so as to improve the connections between various components of the internal assembly 108. In either configuration, the separate cord or other attachment may be removable from the system 100 leaving the system to operate in the configuration illustrated in FIG. 2A. It should be appreciated that the series-series topology illustrated in at least FIG. 2B is shown by way of example and not limitation. Alternative embodiments may be used that employ different circuit topologies, such as series-parallel, parallel-series, parallel-parallel and so on.

The external resonant network coil 256 and the first extension cord coil 286 may be arranged on opposite sides of a first boundary. This first boundary is generally identified by reference number 288 in the schematic illustration of FIG. 2B. Similarly, the internal resonant network coil 256 and the second extension cord coil 290 may be arranged on opposite sides of a second boundary. This second boundary is generally identified by reference number 264 in the schematic illustration of FIG. 2B. In those implementations where the distributed transformer 282 is associated with the external resonant network 120, the skin of the subject within whom the internal assembly 108 is implanted may form the second boundary 264. Here, the first boundary 288 may be a non-skin boundary such as clothing fabric or the like as discussed in more detail herein. In those implementations where the distributed transformer 282 is associated with the internal resonant network 128, the skin of the subject may form the first boundary 288. Here, the second boundary 264 may be a non-skin boundary such as a portion of an implanted medical device or the like as discussed in more detail herein. By way of example and not limitation, the following discussion of the transcutaneous energy transfer system 100 references an implementation where the second boundary 264 is the skin of the subject within whom the internal assembly 108 is implanted.

Figure 3A:
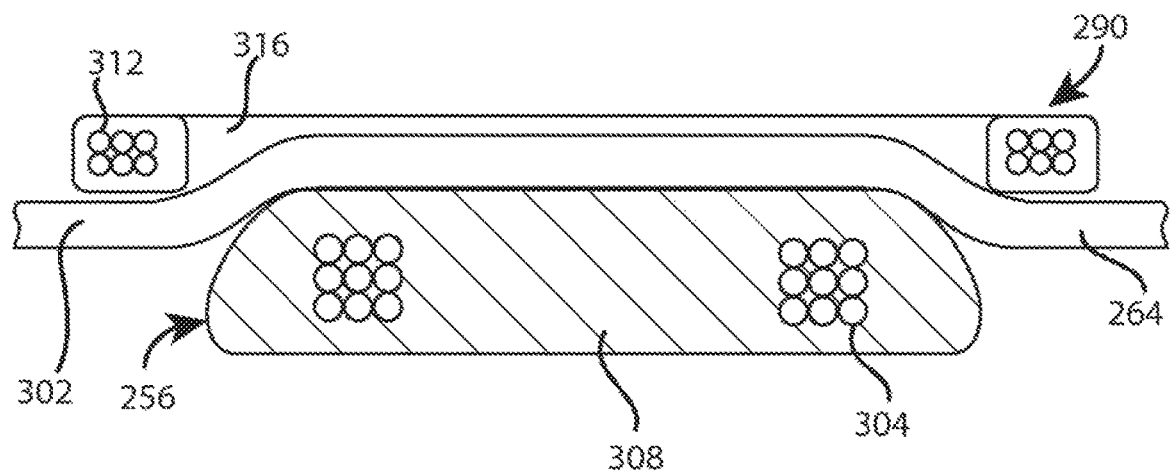
FIGS. 3A and 3B are schematic illustrations of the internal and external coils shown in FIG. 1.
Figure 3B:
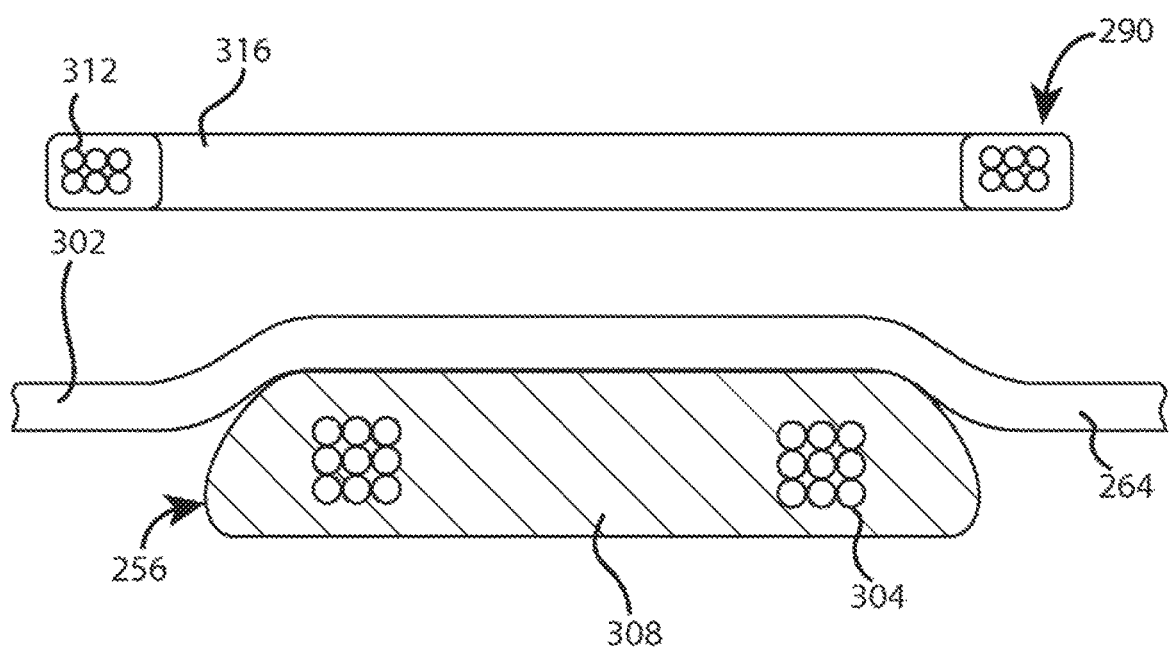

FIGS. 3A and 3B are schematic illustrations of the internal coil 256 coupled to the external resonant network 120. Here, a distributed transformer 282 is in place such that the internal coil 256 couples to the second extension cord coil 290. As mentioned, the distributed transformer 282 may be removable from the system 100. With the distributed transformer 282 removed, the internal coil 256 would couple to the external coil 248 of the external resonant network 120. By way of example, FIGS. 3A and 3B illustrate an implementation where the distributed transformer 282 is associated with the external resonant network 120 such that the first boundary 264 is the skin 302 of the subject. Thus, in FIG. 3A, the internal coil 256 is disposed beneath the skin 302 of the subject and the second extension cord coil 290 is disposed generally adjacent the internal coil 256 on the external side of the skin 302. In FIG. 3B, the internal coil 256 is disposed beneath the skin 264 of a subject and the second extension cord coil 290 is disposed at some distance from the internal coil 256 on the external side of the skin 302. As shown in FIGS. 3A and 3B, the internal coil 256 may have a plurality of conductive windings 304 disposed in a circular insulating member 308. Similarly, the second extension cord coil 290 may have a plurality of conductive windings 312 disposed in an insulating ring 316.

The inductance of each of the coils 256, 290 may be determined by the number, diameter and spacing of the windings 304, 312. The inductive or electromagnetic coupling between the coils 256, 290 is a function of their physical proximity, operating frequencies, coil sizes, and inductances. While the coils shown in FIGS. 3A and 3B have a generally circular shape, other shapes and structures may be used to implement the coils 256, 290, depending on the implementation. For example, the coils 256, 290 may be shaped as a triangle, square, rectangle, pentagon, octagon, and so on. Generally, the coils 256, 290 may be shaped as polygons of any number of sides, which may be equal or unequal in length. The coils 256, 290 may be straight in certain portions and/or curved in certain portions. The coils 256, 290 may be arranged in a planar configuration. Alternatively, the coils 256, 290 may be arranged such that portions of the coils lie in different planes. Although not shown in FIGS. 3A and 3B, the eternal coil 248 and the first extension cord coil 286 may have a similar structure as described above in connection with the internal coil 256 and the second extension cord coil 290.

Turning now to the behavior of the coils of the transcutaneous energy transfer system 100, reference is initially made to the configuration of FIG. 2A where the distributed transformer 282 is not in place. In this configuration, the coils 248, 256 together constitute a loosely coupled transformer, with the external coil 248 acting as a primary winding and the internal coil 256 acting as a secondary winding. The coils 248, 256 and the capacitors 252, 260 with which they may be connected may form a resonant circuit. The coils 248, 256 may be tuned to the same or different resonant frequencies. For example, the coils 248, 256 may be series tuned to a power transmission frequency of about 200 kHz. In the configuration of FIG. 2A, the external coil 248 may induce an electric current in the internal coil 256, which current generally behaves in accordance with the following equation:

$$\frac{V_1}{I_2} = \frac{V_2}{I_1} = \omega \cdot k \cdot \sqrt{L_1 \cdot L_2} \quad (1)$$

In Equation (1), $I_1$ is the current induced in the external resonant network 120. $I_2$ is the current induced in the internal coil network 128. $V_1$ is the voltage across the external resonant network 120. $V_2$ is the voltage across the internal resonant network 128. $\omega$ is the frequency of the voltage across the coils 248, 256, where the coil networks are tuned to the same frequency $\omega$. $L_1$ is the inductance of the external coil 248. $L_2$ is the inductance of the internal coil 256. k is the coupling coefficient.

The relationship described by Equation (1) can be expanded to describe the behavior of the transcutaneous energy transfer system 100 with the distributed transformer 282 in place. Referring again to FIG. 2B, the external coil 248 and the first extension cord coil 290 together constitute a first loosely coupled transformer 280, with the external coil 248 acting as a primary winding and the first extension cord coil 286 acting as a secondary winding. Similarly, the second extension cord coil 290 and the internal coil 256 together constitute a second loosely coupled transformer 284, with the second extension cord coil 290 acting as a primary winding and the internal coil 256 acting as a secondary winding. As shown in FIGS. 3A and 3B, the second extension cord coil 290 and the internal coil 256 may be arranged on opposite sides of the skin 264 of a subject within whom the internal assembly 128 is implanted. In this example, due to the coupling between the coils 290, 256, the second transformer 284 may operate to transfer electric power through a second boundary 264 that includes the skin 302 of the subject. As described in greater detail below, the external coil 248 and the first extension cord coil 286 may be arranged on opposite sides of a non-skin first boundary 288, such as a portion of an article of clothing or a piece of furniture. Thus, due to the coupling between the coils 248, 286, the first transformer 280 may operate to transfer electric power through the non-skin first boundary 288.

In the first transformer 280, the coils 248, 286 and the capacitor 252, and the capacitor network 294 with which they may be connected may form a resonant circuit. Similarly, in the second transformer 284, the coils 290, 256 and the capacitor network 294, and the capacitor 260 with which they may be connected may form a resonant circuit. The coils of the transformers 280, 284 are tuned to the same resonant frequencies. For example, the coils may be series tuned to a power transmission frequency of about 200 kHz. When driven with a time-varying signal, the external coil 248 may induce an electric current in the first extension cord coil 286. This electric current may propagate through the distributed transformer 282 to the second extension cord coil 290, which may then induce an electric current in the internal coil 256. These induced current generally behave in accordance with the following equation:

$$\frac{V2}{I1} = \frac{V1}{I2} = \omega \cdot k1 \cdot k2 \cdot \frac{\sqrt{L1 \cdot L2 \cdot L3 \cdot L4}}{Li} \quad (2)$$

In Equation (2), $I_1$ is the current induced in the external coil 248. $I_2$ is the current induced in the internal coil 256. $V_1$ is the voltage across the external coil 248. $V_2$ is the voltage across the internal coil 256. $\omega$ is the frequency of the voltage across the coils, where the coil networks are tuned to the same frequency $\omega$. $L_1$ is the inductance of the external coil 248. $L_2$ is the inductance of the internal coil 256. $L_3+L_1$ is the inductance of the first extension cord coil 286. $L_4+L_1$ is the inductance of the second extension cord coil 290. $K_1$ is the coupling coefficient between the external coil 248 and the first extension cord coil 286. $K_2$ is the coupling coefficient between the second extension cord 290 and the internal coil 256. Equation (2) applies to embodiments where the distributed transformer 282 is associated with the external resonant network 120 and to embodiments where the distributed transformer 282 is associated with the internal resonant network 128.

Referring to FIGS. 1 and 2A-B, the external assembly 104 includes a power supply 112, which generally provides power in the form of a DC voltage. In some embodiments, the power supply 112 is a portable battery or battery pack providing a DC voltage of between 10 and 18 volts. The external assembly 104 also includes an inverter 116 connected to the power supply 112 via a pair of conductive lines 204, 208. The power supply 112 supplies the DC voltage to the inverter 116, which converts the DC voltage into a high-frequency voltage. The high-frequency voltage is provided to the external resonant network 120 via a pair of conductors 212, 216. A current sensor 220 may be used to sense the electric current flowing within the conductor 216. The current sensor 220 may be configured to sense either or both of the magnitude and phase of the electric current in the conductor 216. A controller 124 connected to the current sensor 220 via a conductor 224 may be used to control the operation of the inverter 116, based on one or more characteristics of the current sensed by the sensor 220. The controller 124 may also be configured to control the voltage $V_{in}$, that is provided by the power supply 112. The external coil network 120, with or without the distributed transformer 282, transfers electric power through the skin 302 of the subject to the internal coil network 128 disposed beneath the skin 302 of the subject.

The internal assembly 108 is disposed beneath the skin 302 of the subject and includes the internal coil network 128. The internal coil network 128 is connected to a power circuit 132 via a pair of conductors 228, 232. The power circuit 132 includes a rectifier 152 that performs full wave rectification of the sinusoidal AC current induced in the internal coil 256 by the external coil 248.

In one embodiment, the rectifier 152 includes four switching elements, which may be provided in the form of diodes or Schottky diodes. During a first half of the AC power cycle, a first pair of diodes provides a conductive path up from ground, through the internal coil 256, and out to conductor line 228. During a second half of the AC power cycle, a second pair of diodes provides a conductive path up from ground, through the internal coil 256, and out to conductor line 228. In this way, the rectifier 152 converts AC power provided by the internal coil network 128 into DC power that can be used by various components of the internal assembly 108.

The power circuit 132 additionally includes a regulator 156 that regulates power supplied by the rectifier 152. The regulator 156 supplies electric power to a controller 136 and other elements via a pair of conductors 240, 244. The controller 136 may control the operation of the heart pump 140. The power conductors 240, 244 also supply electric power to the heart pump 140 through the controller 136. The regulator 156 may be a shunt type regulator that repeatedly charges and discharges a power supply capacitor. In other implementations, other types of regulators, such as a series regulator, may be used. In one embodiment, the power supply capacitor is a component of the charging circuit 144. The voltage across the power capacitor is output via the lines 240, 244 to the controller 136 and to the implanted medical device such as heart pump 140.

During operation, the motor controller 136 drives the heart pump 140 to pump blood through the artificial heart assembly, drawing electric current from the power supply capacitor associated with the charging circuit 144. As current is drawn from the capacitor, the voltage across the capacitor decreases. To replenish the voltage on the capacitor, the power circuit 132 periodically operates in a power supply mode in which electric current generated by the rectifier 152 is provided to the capacitor via the lines 240, 244. When not operating in the power supply mode, the power circuit 132 operates in an idle mode in which current is not supplied to the capacitor.

In the case of shunt type regulator 156 shorting of the resonant secondary 128 may be accomplished by one or more shorting switches 272 that operate to shift the power circuit 132 between the power supply mode and the idle mode. In the power supply mode, the shorting switches 272 open to allow current to flow from the internal resonant network 128, through the rectifier 152, and out to the conductor line 240/244. In idle mode, the shorting switches 272 close to short internal resonant network 128 so that current flows only within resonant network 228 rather than out to the conductor lines 240/244.

The magnitude of the output voltage across the power supply capacitor associated with regulator circuit 156 may control whether the shorting switches 272 are open or closed and thus whether the power circuit 132 operates in the power supply mode or in the idle mode. For example, if the output voltage falls below a certain value, the shorting switches 272 open and the power circuit 132 operates in the power supply mode. When the output voltage rises to a certain value, the shorting switches 272 close and the power supply circuit 132 operates in the idle mode. By selectively supplying current to the power supply capacitor only during certain times (i.e. the power supply mode), the voltage across the capacitor is regulated, or maintained within a predetermined voltage range, such as between about 13 and about 14 volts, for example.

In one embodiment, the shorting switches 272 are implemented as a pair of switching transistors, such as field-effect transistors, though any suitable structure may be used. For example, the shorting switches 272 may be implemented using bipolar junction transistors, and so on. The switching transistors may be configured to short diodes associated with the rectifier 152 in a conductive state and to not do so in a non-conductive state. A switching control circuit may control the conductive state of the switching transistors based on the output voltage across the power supply capacitor associated with the regulator circuit 156. When the output voltage is above a certain value, the control circuit turns on the switching transistors to short diodes associated with the rectifier 152. Here, current flows through the internal resonant network 128 and through the conductive transistors. When the output voltage is below a certain value, the control circuit turns off the switching transistors so that the diodes associated with the rectifier 152 are not shorted. Here, current is allowed to flow from the internal resonant network 128, through the rectifier 152, and out to the conductor line 240/244.

The external assembly 104 may be responsive to the internal assembly shifting between the power supply mode and the idle mode. As mentioned above, the external assembly includes a controller 124 that may be used to control the operation of the inverter 116 based on one or more characteristics of the current sensed by the sensor 220. In this regard, the controller 124 may change the frequency at which the inverter 116 operates to conserve electric power during the idle mode. During the idle mode, when electric current is not being supplied to the capacitor associated with the charging circuit 144, the power transmitted to the internal coil 256 by the external coil 248 is reduced in order to conserve the power of the power supply 112. This is accomplished by changing the frequency at which the inverter 116 operates.

As noted above, the internal and external coils 248, 256 may be tuned to a power transmission frequency, such as about 200 kHz. Consequently, when it is desired to transmit power to the internal coil 256, the inverter 116 is operated at the power transmission frequency to which it is tuned. However, when it is not necessary to transmit a significant amount of power, such as during the idle mode above, the frequency of the inverter 116 is changed. The frequency at which the inverter 116 operates during the power-supply mode may be changed to an odd sub-harmonic of that frequency during the idle mode. For example, the idle mode frequency may be $\frac{1}{3}$, $\frac{1}{5}$, $\frac{1}{7}$, $\frac{1}{9}$ of the power supply mode frequency. The amount of power transmitted to the internal coil 256 varies with the idle mode frequency, with less power being transmitted at the seventh subharmonic (i.e. $\frac{1}{7}$ of the power supply mode frequency, or 28.6 kHz if the power transmission frequency is 200 kHz) than at the third subharmonic (i.e. $\frac{1}{3}$ of the power supply mode frequency). Since odd subharmonics of a fundamental frequency still contain, in accordance with Fourier analysis, some components of the fundamental frequency, using an odd subharmonic of the power supply mode frequency during idle mode will still result in some power being transmitted to the internal coil 256, which is generally desirable.

Figure 4A:
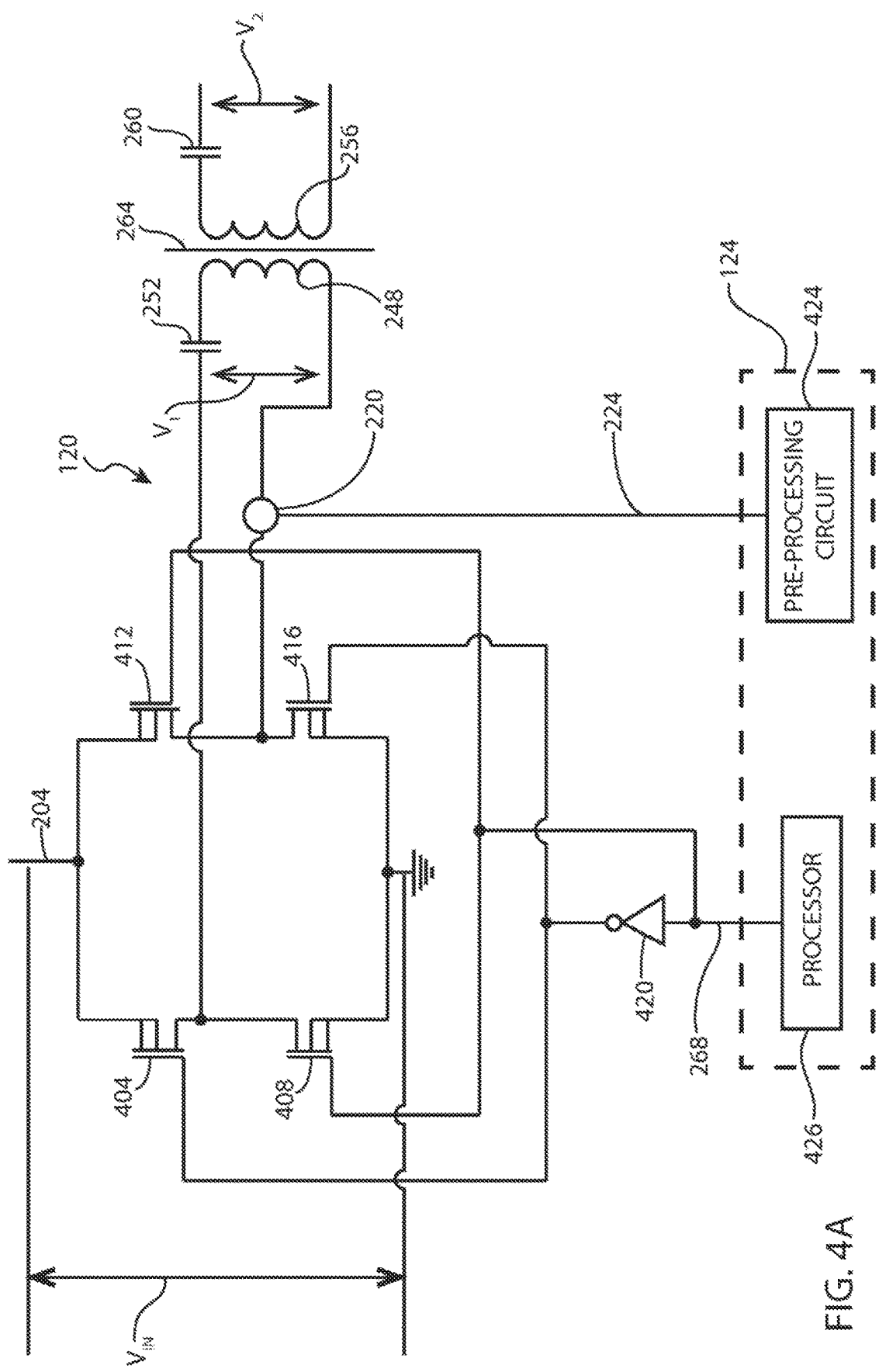
FIG. 4A is a circuit diagram that shows one implementation of the inverter shown in FIG. 1.
Figure 4B:
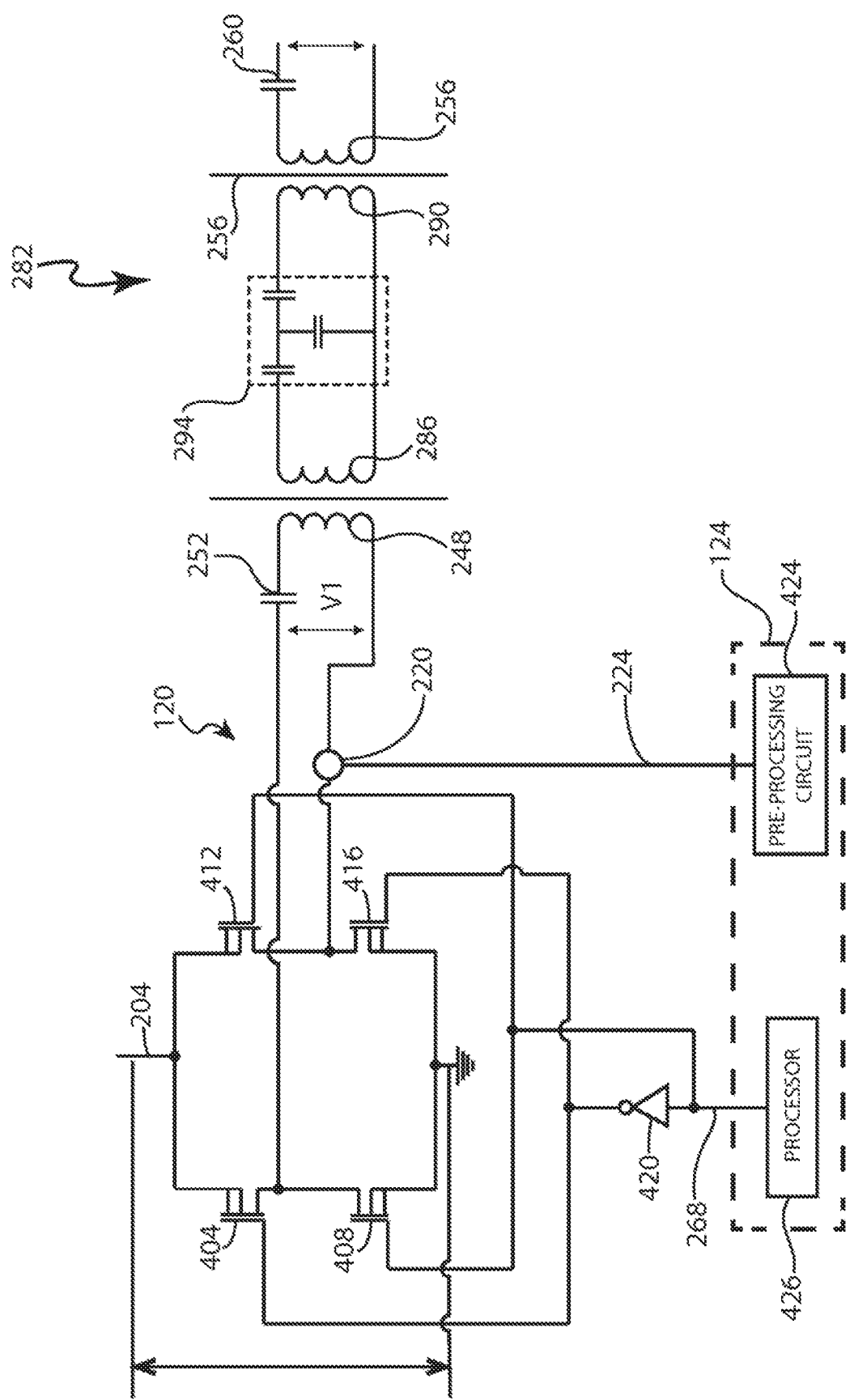
FIG. 4B is a circuit diagram that shows one implementation of the inverter shown in FIG. 1 that includes a distributed transformer.

FIGS. 4A-B are circuit diagrams that show one implementation of the inverter 116. FIG. 4A corresponds to the circuit diagram of FIG. 2A where a distributed transformer 282 is not in place. FIG. 4B corresponds to the circuit diagrams of FIG. 2B where a distributed transformer 282 is in place. As shown in FIGS. 4A-B, the inverter 116 may comprise four transistors 404, 408, 412, 416, which may be metal oxide field-effect transistors (MOSFETs), connected in an H-bridge configuration. The four transistors 404, 408, 412, 416 may drive the external coil network 120 through the conductor 212. Each of the transistors 404, 408, 412, 416, may be controlled by a respective high-frequency drive signal provided on the conductor 268, with two of the drive signals being 180° out of phase, or complemented, with respect to the other two via an inverter 420. The drive signals may be 50% duty cycle square waves provided at a frequency of about 200 kHz, for example. Although a particular type of DC-to-AC converter has been described above, any type of electronic switching network that generates a high-frequency voltage may be used. For example, as an alternative to the H-bridge configuration, the inverter 116 may have transistors arranged in a voltage source half bridge configuration or in a current source configuration or in a class-DE amplifier voltage source configuration.

The inverter 116 may be connected to the controller 124 to control the operation of the inverter 116 based on one or more characteristics of the current sensed by the sensor 220. Referring to FIGS. 2A-B, the inverter 116 may be connected to the controller 124 through the conductor 268. The controller 124, in turn, may be connected to the current sensor 220 via the line 224. Referring to FIGS. 4A-B, controller 124 may include certain pre-processing circuits 424 that operate on the current signal and a processor 426 that receives input generated by the preprocessing circuit 424 based the current signal. The pre-processing circuits 424 may include circuits that accomplish such functions as current to voltage conversion, decoupling detection, interference detection, and shorting/un-shorting detection, and so on.

In one embodiment, the pre-processing circuit 424 may be configured to generate a voltage that is indicative of the magnitude of the electric current flowing through the external coil 248, where the current flowing through the external coil 248 is proportional to the voltage across the internal coil 256. During the idle mode, the shorting switches 272 are closed, which causes the voltage across the internal coil network 128 to significantly decrease. This voltage decrease causes the current in the external coil 248 to be significantly decreased in accordance with Equation (1) when the distributed transformer 282 is not in place, and in accordance with Equation (2) when the distributed transformer 282 is in place. Consequently, the voltage generated by the pre-processing circuit 424 decreases significantly when the power circuit 132 is in the idle mode.

The output of the controller 124 may be configured to drive the inverter 116 at different frequencies depending on the voltage received from the pre-processing circuit 424. In one embodiment, the controller 124 output may be provided by the processor 426, which provides output responsive to input from the pre-processing circuit 424. When the preprocessing circuit 424 generates a voltage that is not decreased indicating that the power circuit 132 is in power supply mode, the output of the controller 124 may drive the inverter 116 at a first frequency, such as 200 kHz. When the pre-processing circuit 424 generates a voltage that is decreased indicating that the power circuit 132 is in idle mode, the output of the controller 124 may drive the inverter 116 at a second frequency that is an odd sub-harmonic of the frequency generated during the power supply mode.

Distributed Transformer Implementations

Figure 5:
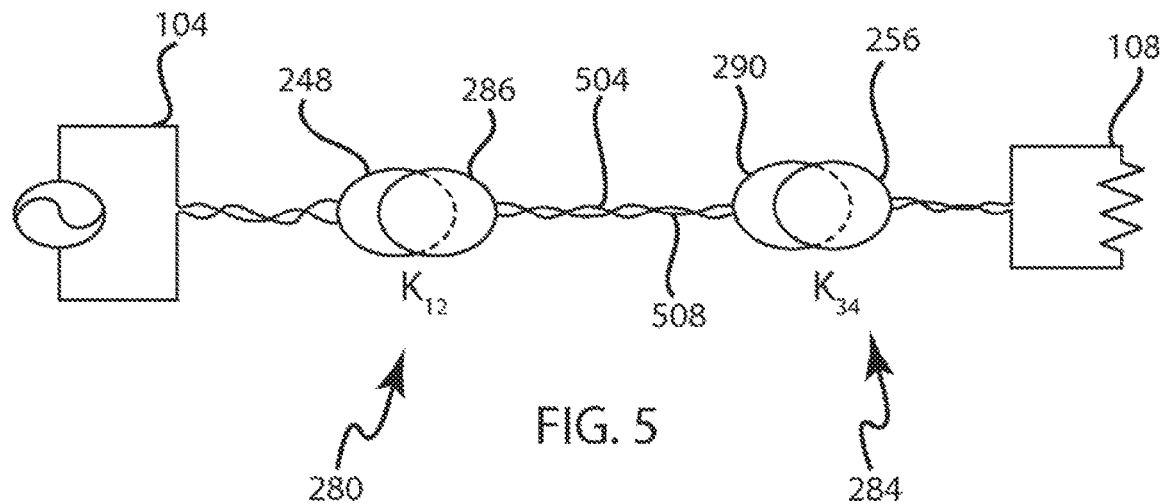
FIG. 5 is diagram of a physical layout of a distributed transformer in accordance with embodiments discussed herein.
Figure 6:
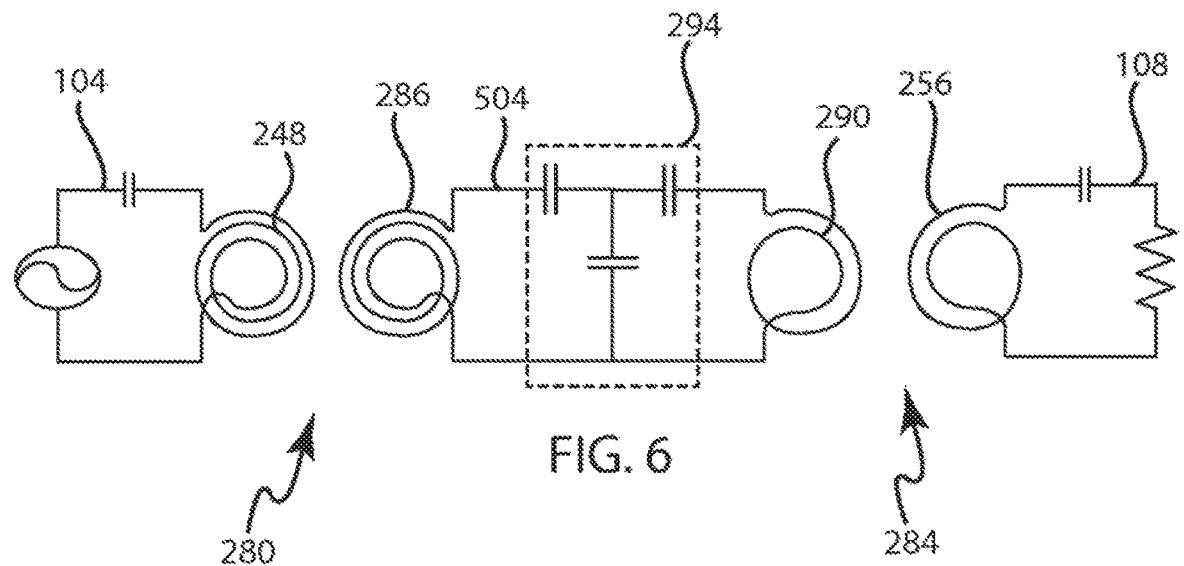
FIG. 6 is an example circuit diagram for the distributed transformer shown in FIG. 5.

Distributed transformer implementations may include a cord or other attachment that couples to the external resonant network 120. FIG. 5 is a diagram of a physical layout of a distributed transformer implementation that includes such an "extension cord" component coupled to various other components. Certain components illustrated in other figures are omitted from FIG. 5 to simplifying the drawing. Specifically, FIG. 5 shows the external coil 248, while other components of the external assembly 104 are omitted. Similarly, FIG. 5 shows the internal coil 256, while other components of the internal assembly 108 are omitted. The distributed transformer implementation of FIG. 5 also includes an extension cord 504 that extends between the external coil 248 and the internal coil 256. The extension cord 504 includes the first extension cord coil 286 and the second extension cord coil 290. The extension cord capacitor network 294 is omitted to simplify to drawing. FIG. 6 is a circuit diagram of the extension cord embodiment shown in FIG. 5.

Figure 7B:
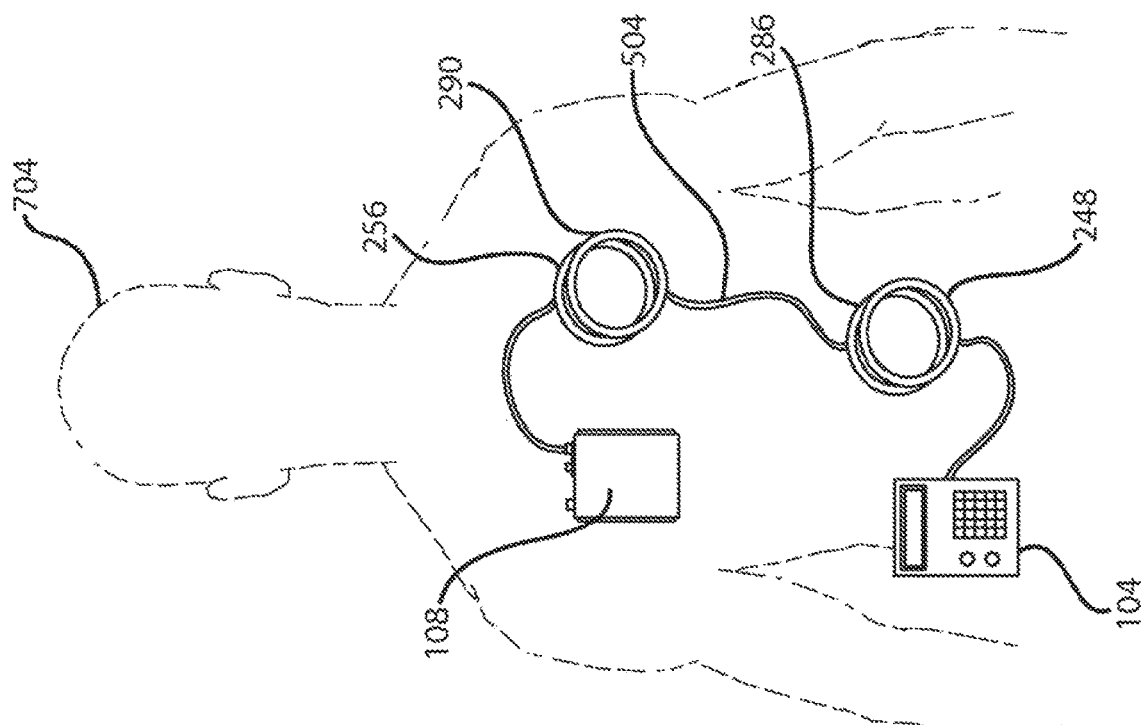
FIG. 7B is a diagram of an implementation of the wireless power transfer system of FIG. 1 that includes the distributed transformer of FIG. 5.

The extension cord 504 may be used to extend the distance between the coil 248 of the external resonant network 120 and the coil 256 of the internal resonant network 128. The extension cord 504 may be a separate component that can be inserted between the external coil 248 and the internal coil 256, as needed. Because power transfer between the coils occurs wirelessly (i.e. physical contact between conductive components is not needed), the components of the extension cord 504 may be completely enclosed within an external packing. More specifically, the extension cord 504 may include an insulating material (such as shown in FIG. 7B) that encloses the extension cord coils 286, 290 and the extension cord capacitor network 294, as well as conductive wires 508 that extend between the coils 286, 290 and the capacitor network 294. In order to extend the distance between the external coil 248 and the internal coil 256, the extension cord 504 may be arranged such that the first extension cord coil 286 is placed in operative association with the external coil 248. Similarly, the second extension cord coil 290 may be placed in operative association with the internal coil 256. In this configuration, the external coil 248 and the internal coil 256 may be separated by a distance generally up to the length of extension cord 248.

Figure 7A:
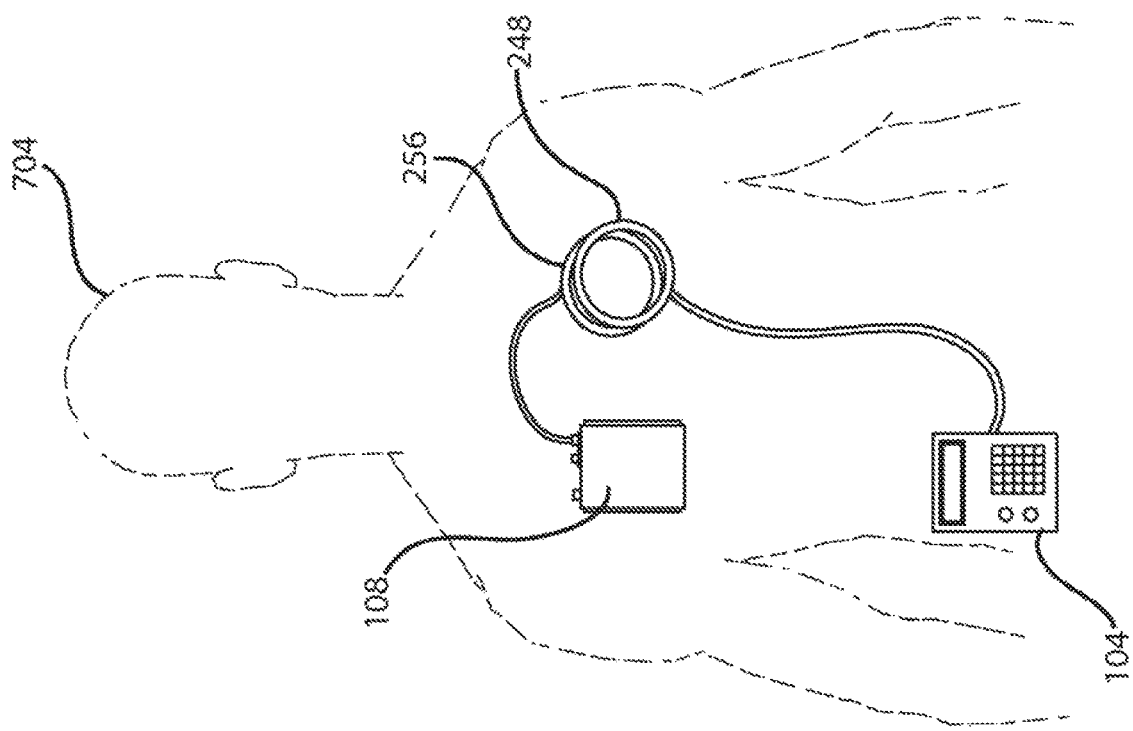
FIG. 7A is a diagram of an implementation of the wireless power transfer system of FIG. 1 that does not include a distributed transformer.

FIGS. 7A-7B are schematic diagrams of an implementation of the wireless power transfer system 100 implemented in connection with an example subject 704. FIGS. 7A-7B generally illustrate the use of an extension cord 504 to extend the distance between the external coil 248 and the internal coil 256. Specifically, the diagram of FIG. 7A illustrates the transcutaneous energy transfer system 100 without an extension cord in place; whereas, the diagram of FIG. 7B illustrates the transcutaneous energy transfer system 100 with an extension cord 504 in place. Without the extension cord 504, placement of the external coil 248 is limited to be being located generally adjacent to the internal coil 256, which is disposed in a fixed location within the subject 704. With the extension cord 504, the external coil 248 may be placed at various locations adjacent to the body of the subject 704.

Stated another way, the extension cord 504 effectively translates the point on the body of the subject 704 where the power transfer occurs from the fixed point adjacent the internal coil 256 to any point that is reachable by the extension cord 504. Without the extension cord 504, the external coil 248 is placed against or generally adjacent to the point on the body where the internal coil 256 is located, such as the left side of the chest as shown in FIG. 7A. With the extension cord 504, the external coil 248 can be placed against or generally adjacent to various points on the body, such as the back, the lower abdomen, the arm, etc. By way of example, FIG. 7B illustrates an arrangement of the extension cord 504 that allows the external coil 248 to be placed against or generally adjacent to the lower abdomen of the subject 704.

Figure 8:
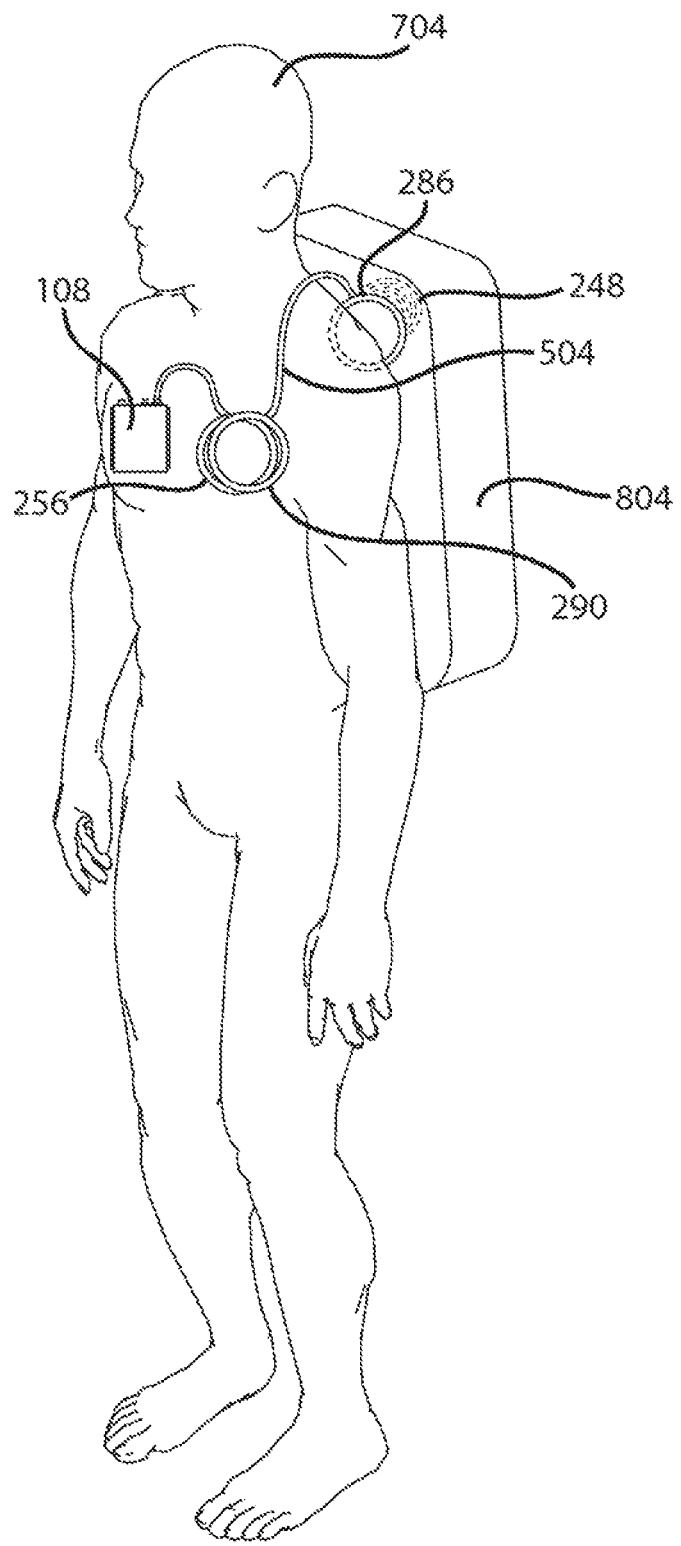
FIG. 8 is a diagram of the distributed transformer implementation of FIG. 5 where the power source is included within a backpack worn by the subject.

By translating the point on the body of the subject 704 where power transfer occurs, the extension cord 504 allows the external assembly 104 or a substantial portion thereof to be placed in or otherwise associated with an object or item that is used by the subject 704 within whom the internal assembly 108 is implanted. For example, as shown in FIG. 8, the external assembly 104 may be included within a backpack 804 worn by the subject 704. Here, the extension cord 504 is arranged such that the second extension cord coil 290 is placed against or generally adjacent to the chest, where the internal coil 256 is located. The length of the extension cord 504 extends from the chest, over the shoulder, and down the back. The first extension cord coil 286 thus rests against or is generally adjacent to a point on the upper back of the subject 704. In this way, the extension cord 504 effectively translates the point on the body where the power transfer occurs from the chest to the back. Power transfer may then be effected by placing the external coil 248 against or generally adjacent to the back of the subject 704. In this arrangement, the external assembly 104 including the external coil 248 may be placed in an object, such as the backpack 804 shown in FIG. 8, which can conveniently rest against the back of the subject 704. The various components may be arranged such that when the subject 704 wears the backpack 804, the external coil 248 is aligned with the first extension cord coil 286 so as to enable efficient power transfer. In other configurations, the external assembly 104 including the external coil 248 may be disposed in other objects such as in a chair 904, as illustrated in FIG. 9.

As mentioned, the distributed transformer configuration of the system 100 allows power to be transferred across both a skin boundary and a non-skin boundary. In one embodiment, the loosely coupled transformer 284 formed by the second extension cord coil 290 and the internal coil 256 transfers power across a skin second boundary 264; and the loosely coupled transformer 280 formed by the external coil 248 and the first extension cord coil 286 transfers power across a non-skin first boundary 288. FIGS. 8 and 9 illustrate this aspect of the distributed transformer configuration. In FIG. 8, the non-skin first boundary 288 includes at least a portion the backpack 804. Here, the external coil 248 is contained within the backpack 804 and the first extension cord coil 286 is outside of the backpack 804. Thus, due to the coupling between the coils 248, 286, the transformer 280 may operate to transfer electric power through a non-skin first boundary 288 that includes the fabric of the backpack 804.

Figure 9:
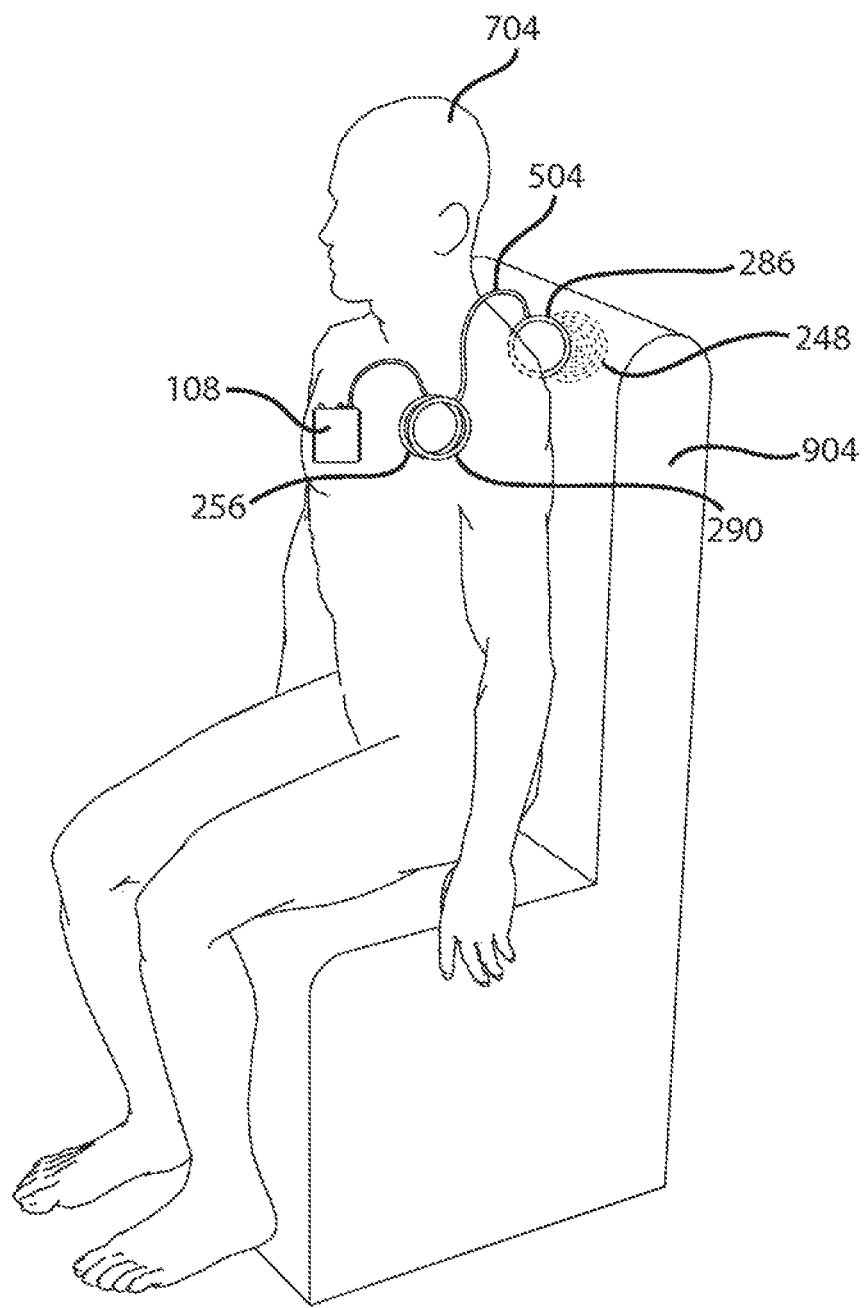
FIG. 9 is a diagram of the distributed transformer implementation of FIG. 5 where the power source is included within a chair used by the subject.

In FIG. 9, the non-skin first boundary 288 includes at least a portion of the chair 904. Here, the external coil 248 is contained within the interior of the chair 904 and the first extension cord coil 286 is outside of the chair 904. Thus, due to the coupling between the coils 248, 286, the transformer 280 may operate to transfer electric power through a non-skin first boundary 288 that includes the fabric of the chair 904.

Quality of life improvements or other conveniences can be achieved when the extension cord 504 is used and one or more external assemblies 104 are placed in objects or items such as a backpack 804 or a chair 904 used by the subject 704. By placing an external assembly 104 in a backpack 804, the mobility of the subject 704 can be improved. If the subject 704 wants to move about, the subject 704 need only put on the backpack 804 so as to remain connected to an external assembly 104 for continuous power transfer. Because the various coils are aligned for power transfer through their arrangement in the extension cord 504 and in the backpack 804, the subject 704 need not bother with aligning the external coil 248 to the internal coil 256 when he or she puts on the backpack 804. Similarly, with an external assembly 104 disposed in a chair 904, the subject 704 need only sit in the chair so as to remain connected to an external assembly 104 for continuous power transfer. Because the various coils are aligned for power transfer through their arrangement in the extension cord 504 and in the chair 804, the subject 704 need not bother with aligning the external coil 248 to the internal coil 256 when he or she sits in the chair 904.

Figure 10B:
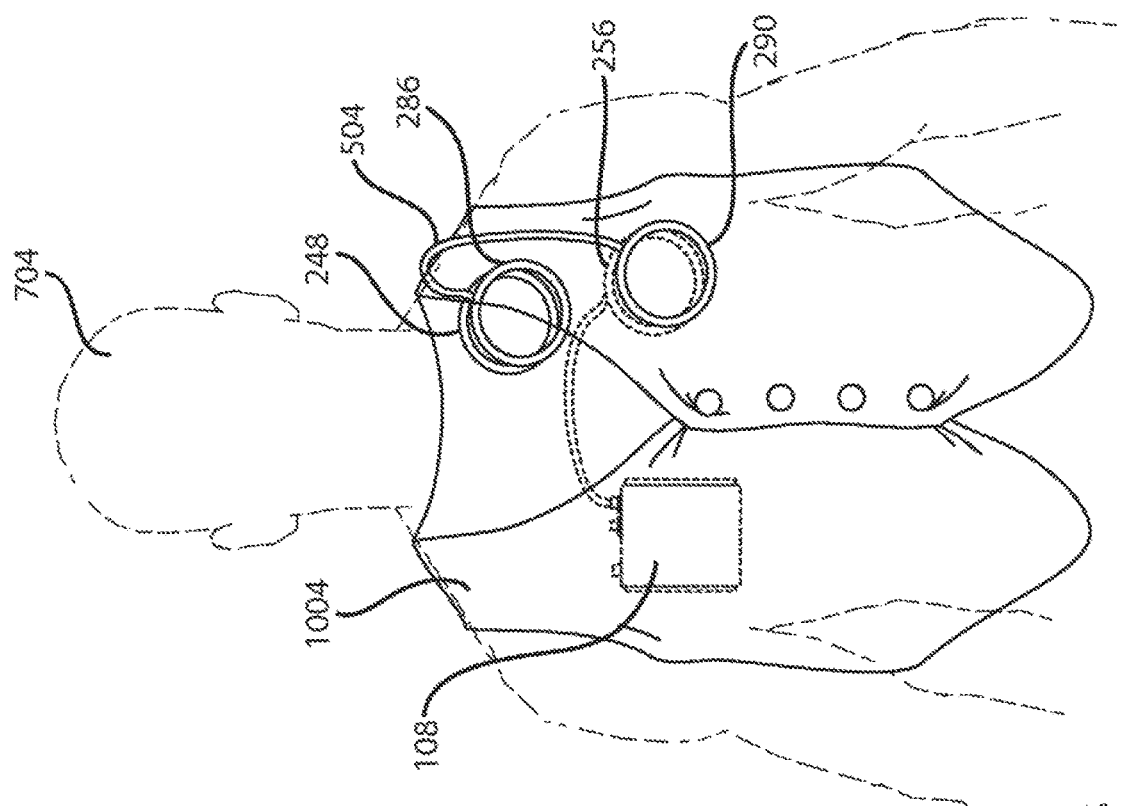
FIGS. 10A-B are illustrations of the distributed transformer of FIG. 5 included within a vest or shirt in accordance with embodiments discussed herein.
Figure 10A:
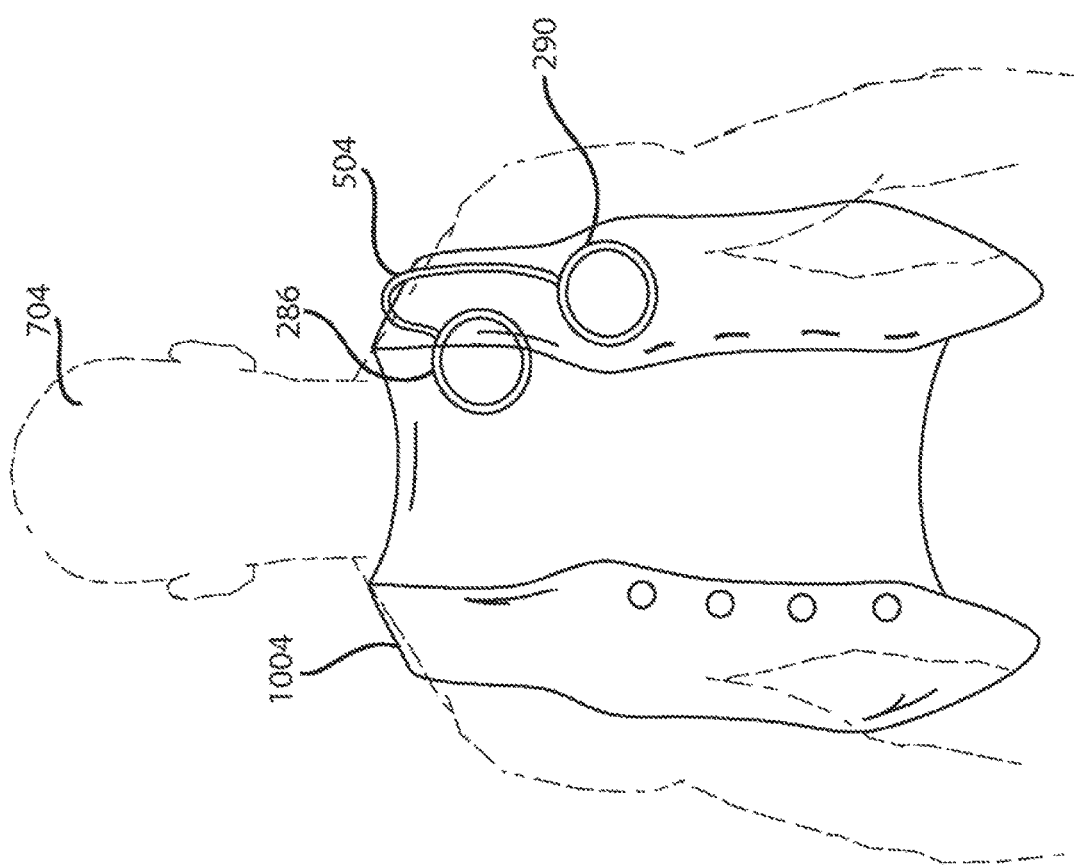

For further convenience, the extension cord 504 may be incorporated within a shirt or vest 1004 worn by the subject 704, such as illustrated in FIGS. 10A-10B. The extension cord 504 may by incorporated in the shirt or vest 1004 in a position that maintains the proper alignment for the first and second extension cord coils 286, 290. Specifically, the extension cord 504 may be incorporated in the shirt or vest 1004 such that the second extension cord coil 290 is in operative association with the internal coil 256 when the subject 704 wears the shirt or vest 1004. Further, the extension cord 504 may be incorporated in the shirt or vest 1004 such that the first extension cord coil 286 is conveniently placed for operative association with an external coil 248 incorporated in an object used by the subject 704, such a backpack 804 or a chair 904. For example, as illustrated in FIGS. 10A-10B, the extension cord 504 may be incorporated in the shirt or vest 1004 such that the second extension cord coil 290 is located against or generally adjacent to the chest, where the internal coil 256 is located. The length of the extension cord 504 may extend from the chest, over the shoulder, and down the back such that the first extension cord coil 286 rests against or is generally adjacent the upper back of the subject 704. The extension cord 504 may be incorporated into the vest or shirt 1004 by any convenient method, such as sewing.

In use, the subject 704 may put on the shirt or vest 1004, put the backpack 804 on over the shirt or vest 1004, and move about without having to bother with aligning the various power transfer coils. When the subject 704 wishes to rest, he or she may simply take off the backpack 804 and sit in the char 904. Here, the external assembly 104 in the chair 904 takes over from the external assembly 104 in the backpack 804 and, again, the subject need not bother with aligning the various power transfer coils. Here, the transformer 280 may operate to transfer electric power through a non-skin first boundary 288 that includes the fabric of the shirt or vest 1004, as well as the fabric of the backpack 804 or the chair 904.

In some implementations, the backpack 804 may be waterproof so as to allow the subject to go swimming or to otherwise be immersed in water. Here, the electronic components of the external assembly 104 that must remain dry are enclosed within a waterproof boundary formed by the backpack 804. Power transfer can occur despite the presence of water because all electric currents in the system flow in a waterproof enclosure. Specifically, electric currents flow in either the waterproof backpack 804 or within a waterproof area formed by the insulating material that encloses the circuit components of the extension cord 504. Thus, in one possible arrangement, the subject 704 may put on the shirt or vest 1004, put the backpack 704 on over the shirt or vest 1004, and go swimming.

Figure 11A:
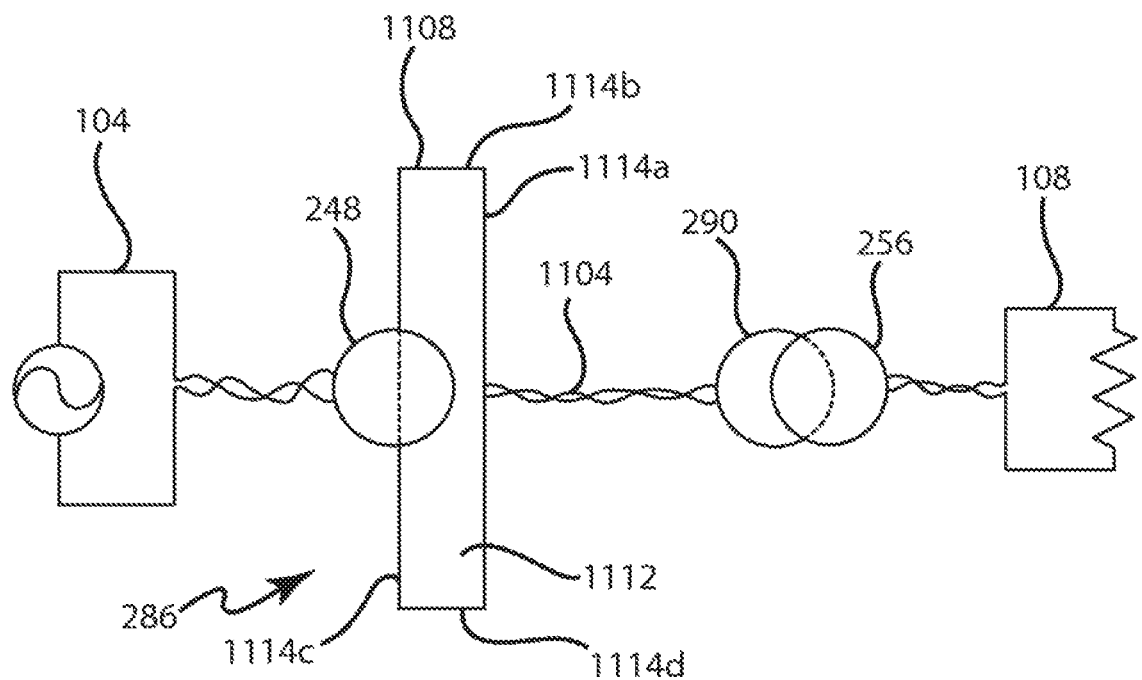
FIG. 11A is a diagram of a physical layout of a distributed transformer embodiment that includes a rectangular inductive coil that forms an inductive track.
Figure 11B:
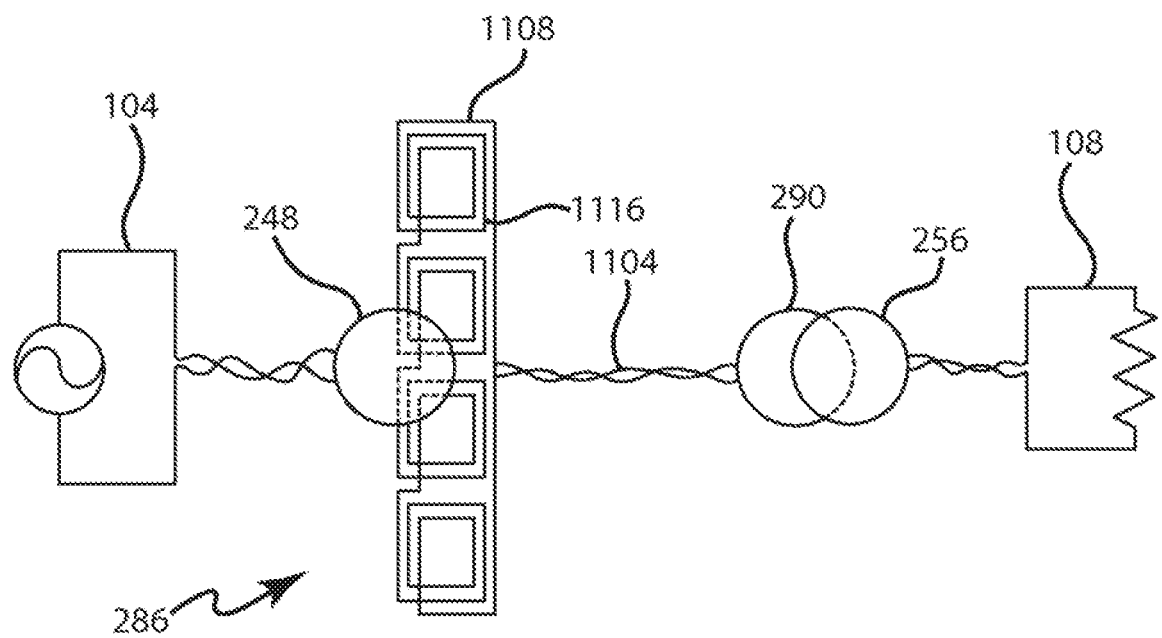
FIG. 11B is diagram of a physical layout of a distributed transformer embodiment that includes a inductive track formed by an array of coils.
Figure 12:
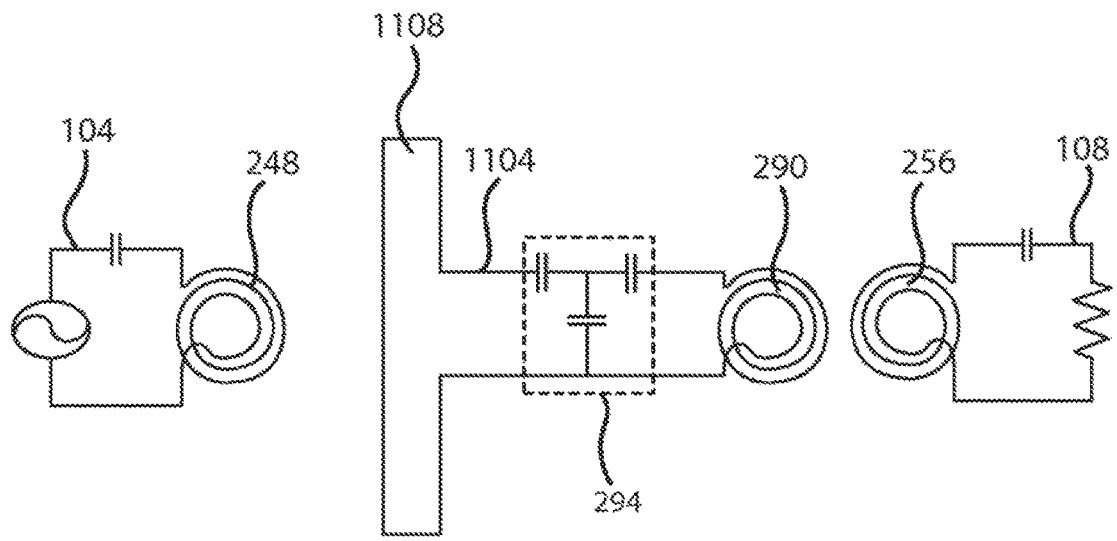
FIG. 12 is a circuit diagram for the distributed transformer embodiments shown in FIGS. 11A-B.

FIGS. 11A-11B are diagrams of a physical layout of an additional distributed transformer implementations that include an "extension cord" component 1104 that features the first extension cord coil implemented as a generally rectangular or rectilinear inductive track or sequentially connected coils that form a track 1108. Certain components illustrated in other figures are omitted from FIGS. 11A-11B to simplifying the drawing. Specifically, FIGS. 11A-11B show the external coil 248, while other components of the external assembly 104 are omitted. Similarly, FIGS. 11A-11B show the internal coil 256, while other components of the internal assembly 108 are omitted. The distributed transformer implementations of FIG. 11A-11B also include an extension cord 1104 that extends between the external coil 248 and the internal coil 256. The extension cord 1104 includes the first extension cord coil 286 that is implemented as a rectangular inductive track or sequentially connected coils that form a track 1108. The extension cord 1108 additionally includes a second extension cord coil 290. The extension cord capacitor network 294 is omitted to simplify to drawing. FIG. 12 is a circuit diagram of the extension cord embodiments shown in FIGS. 11A-11B.

Figure 13A:
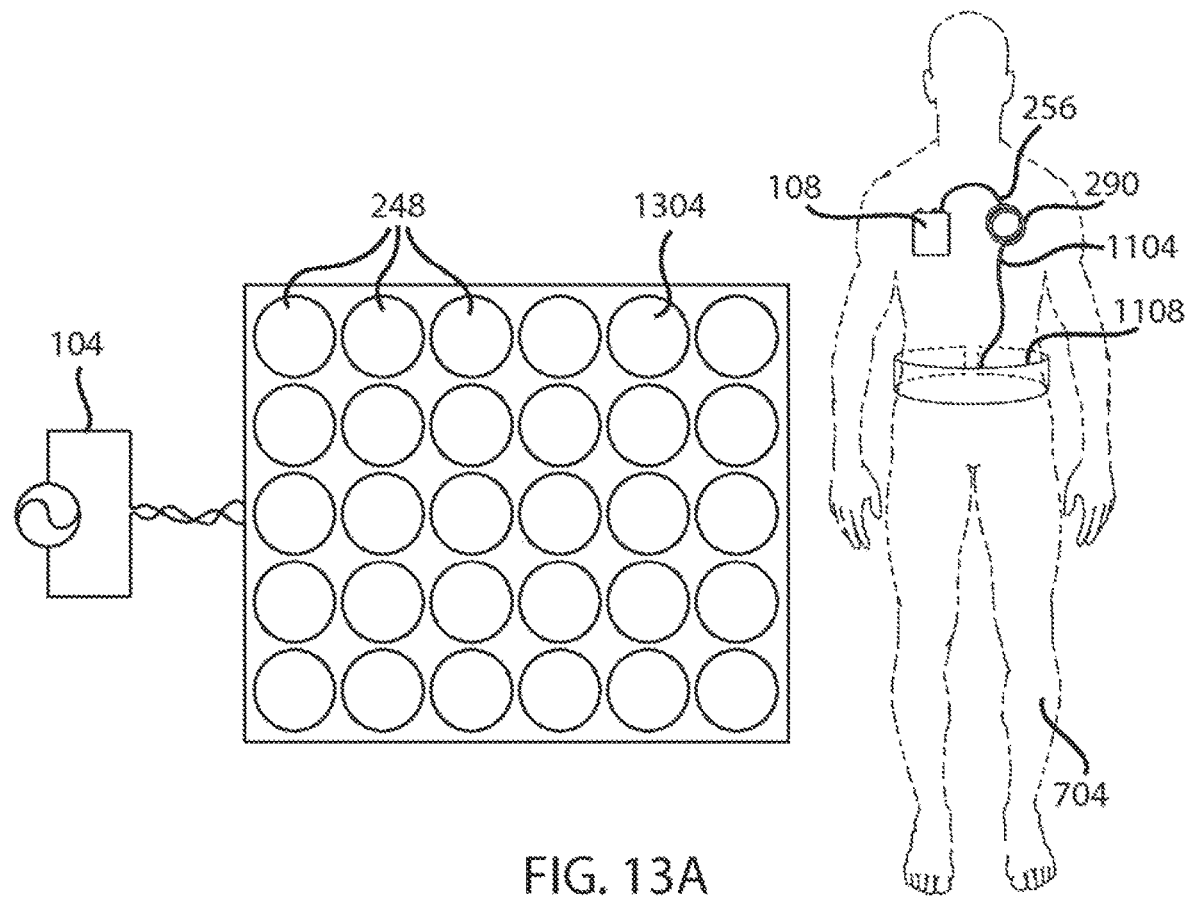
FIG. 13A is a schematic diagram for an array of coils for use in combination with the distributed transformer embodiments shown in FIGS. 11A-B.
Figure 13B:
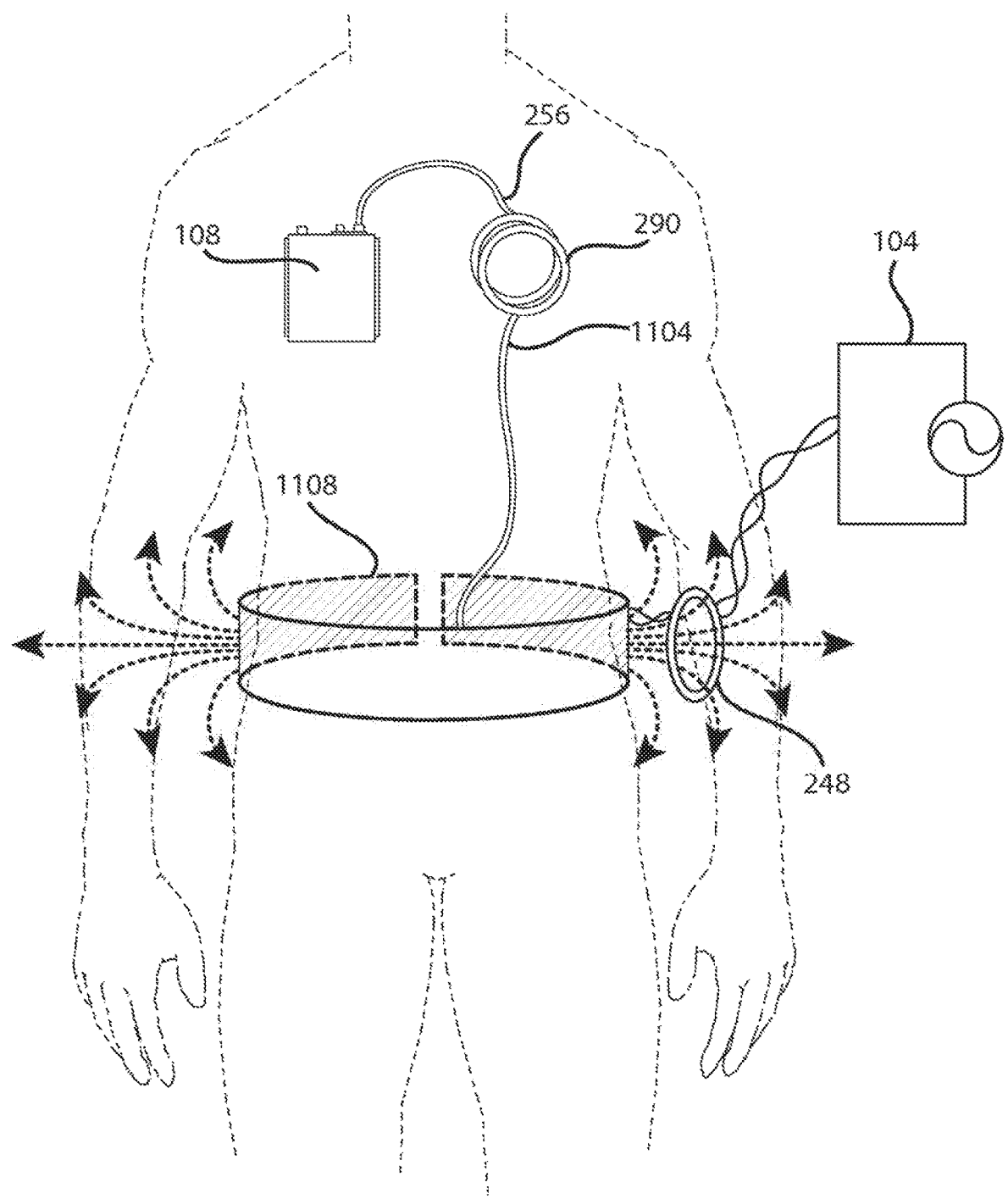
FIG. 13B is an illustration of coupling established between an inductive track and an external coil in accordance with embodiments discussed herein.

The extension cord 1104 shown in FIG. 11A-11B features a rectangular inductive track or sequentially connected coils that form a track 1108 that is configured to be wrapped around the waist of a subject 704, such as shown in FIG. 13A. The track 1108 may include a single inductive track 1112, such as shown in FIG. 11A. In this embodiment, current travels along conductors 1114a-d that form the perimeter or edges of the inductive track 1112 and the interior regions of the single inductive track 1112 that are adjacent the conductors 1114a-d are non-conductive. Alternatively, the track 1108 may include a plurality of coils 1116 arranged along the length of the track 1108, such as shown in FIG. 11B. FIG. 13B is an illustration of the coupling that is established between the track 1108 and an external coil 248 that is positioned adjacent to a given point on the track 1118 and oriented to be at least not perpendicular with a plane defined by the width of the track 1118. Whether the track 1108 is a generally rectangular or rectilinear inductive track 1112 or sequentially connected coils 1116 that form a track, the track 1108 may be configured to provide a plurality of power transfer points along the length of the track 1108. More specifically, power transfer may be affected by placing the inductive track 1108 in contact or in close proximity to an external coil 248 at any point along the track. This aspect of the extension cord 1104 may allow the cord 1104 to be used in combination with an array 1304 of external coils 248, such as illustrated in FIG. 13A. Here, each coil 248 may be configured to transfer power from an external assembly 104. To conserve power, the external assembly 104 may be configured to provide power only to those coils 248 in the array 1304 that are in close proximity to the inductive track 1108 worn by the subject 704.

Figure 14A:
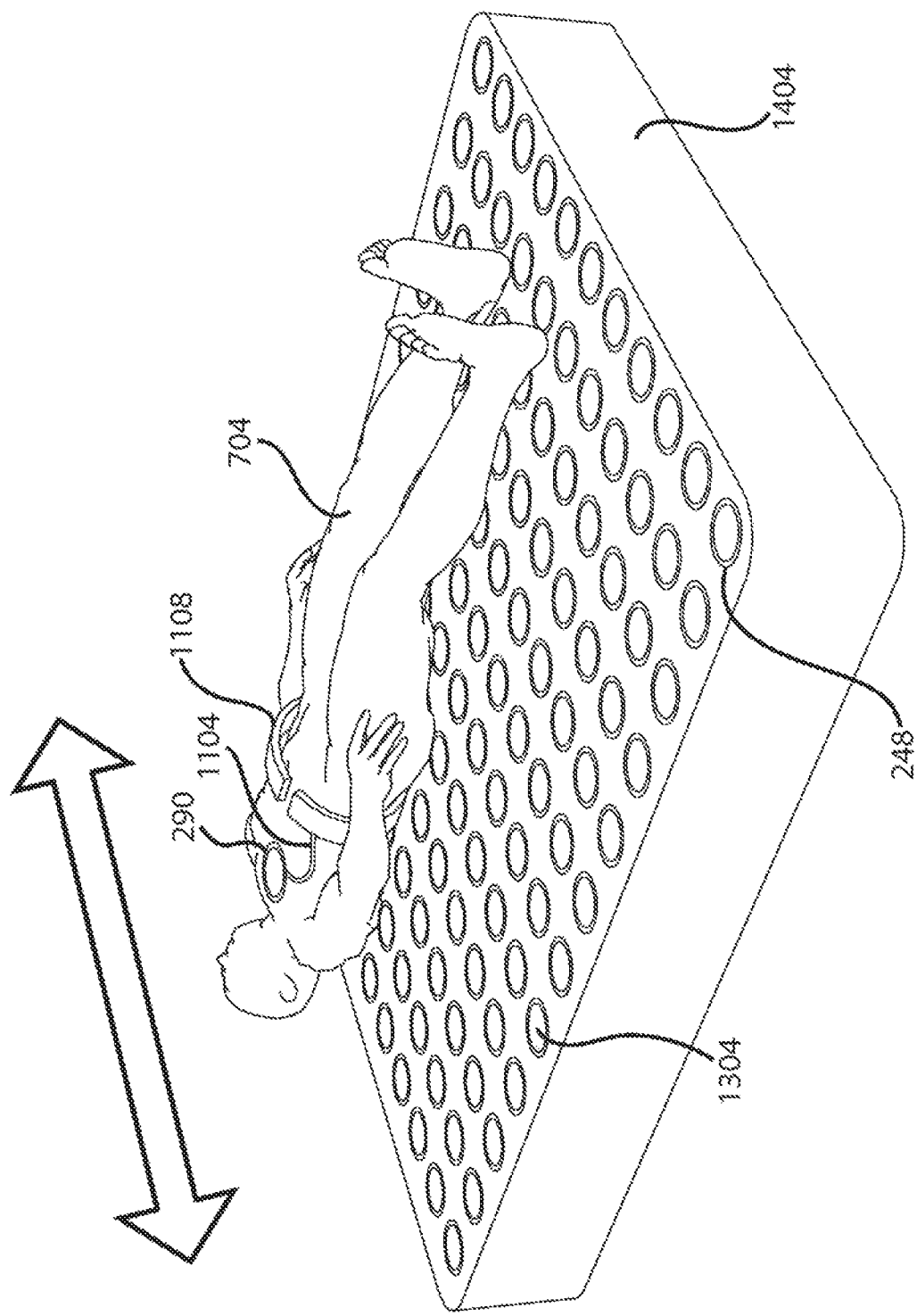
Figure 15:
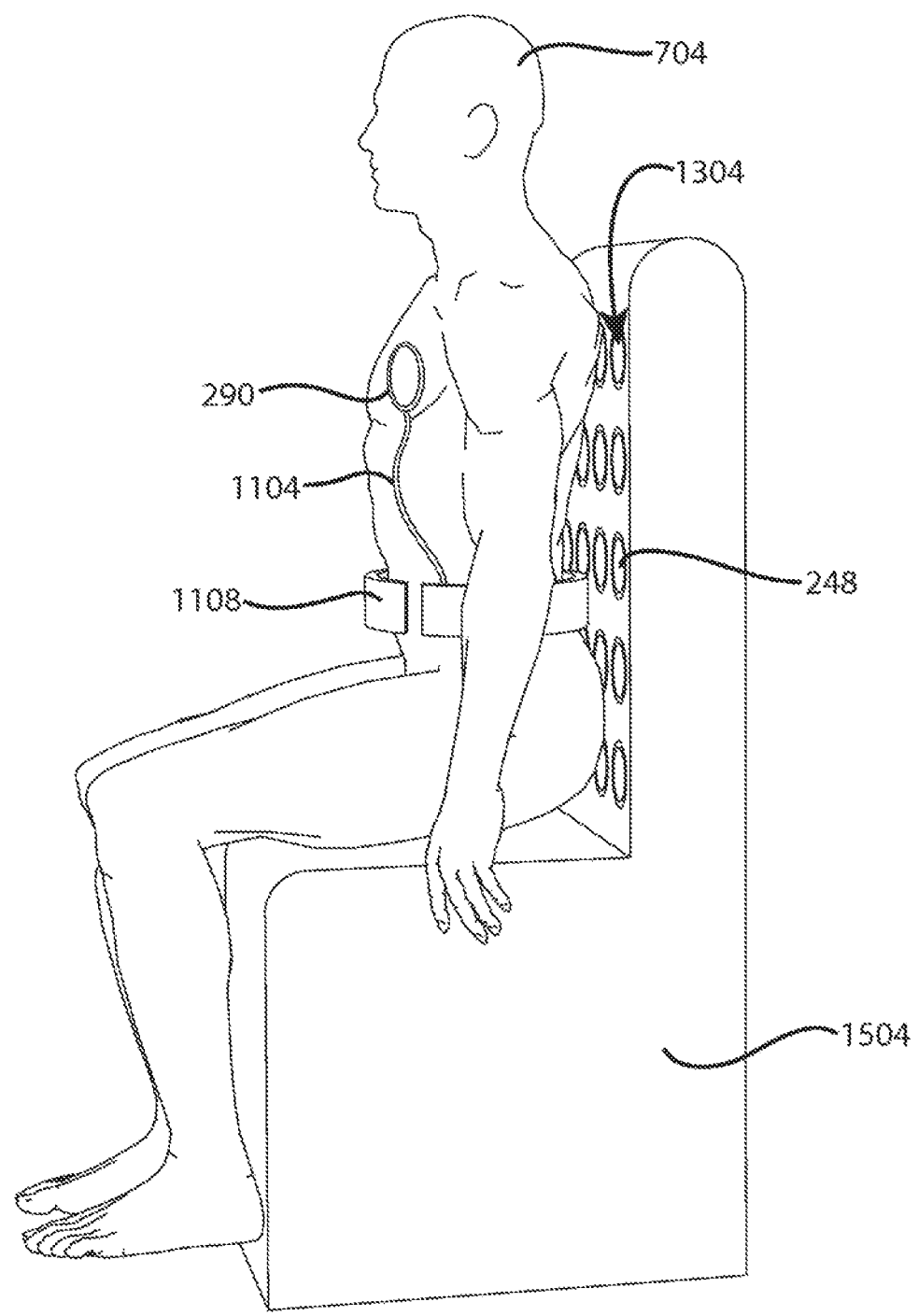
FIG. 15 is an illustration of the distributed transformer embodiments of FIGS. 11A-B used in connection with array of coils that is included within a chair.
Figure 16A:
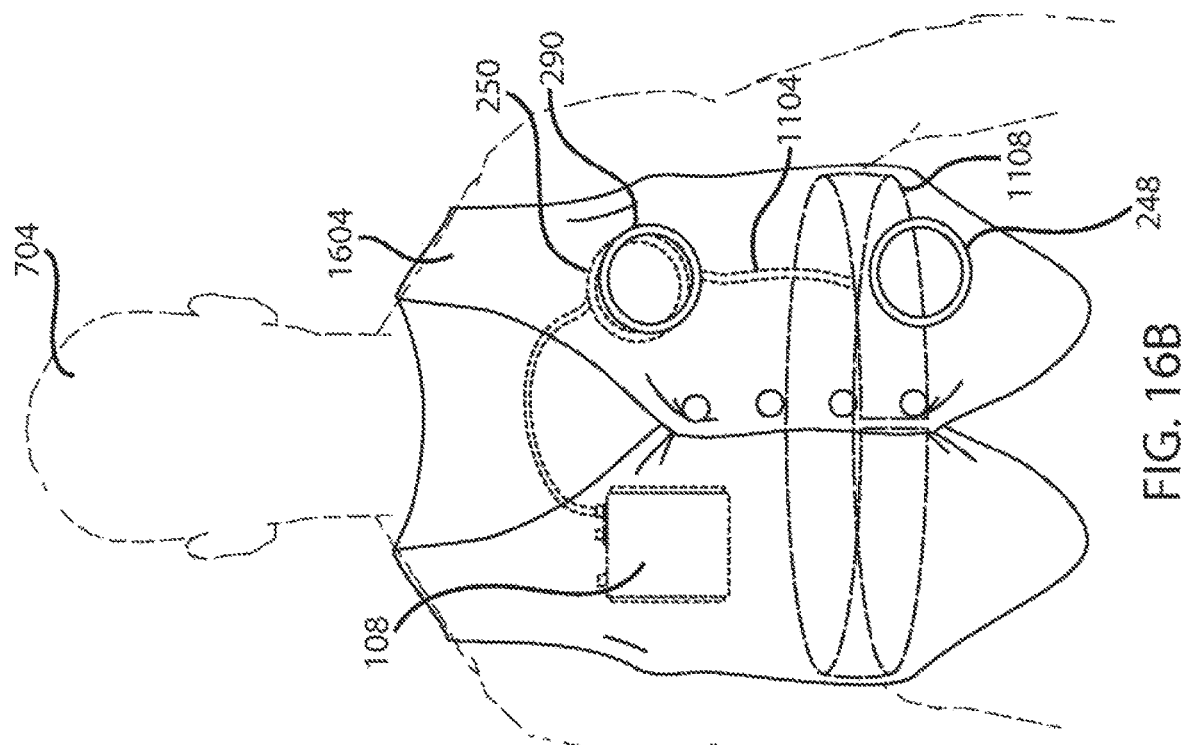
FIGS. 16A-B are illustrations of the distributed transformer of FIGS. 11A-B included within a vest or shirt in accordance with embodiments discussed herein.
Figure 16B:
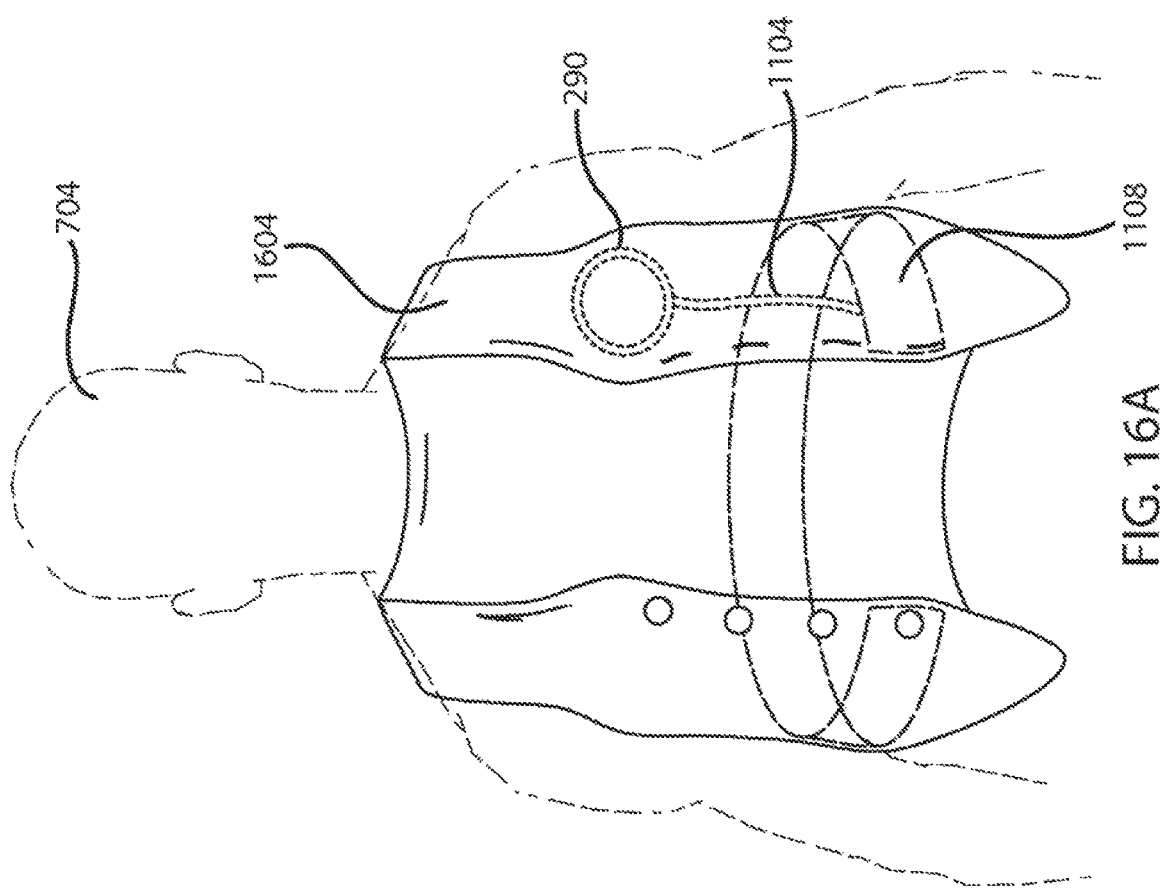

FIGS. 14A-14B illustrate an implementation of the system 100 that features an array 1304 of coils 248 that are incorporated in a mattress 1404. Here, the array 1304 of coils 248, along with possibly the remainder of the external assembly 104, is disposed within the interior of the mattress 1404. The subject 704 receives a power transfer from the external assembly 104 by lying on the mattress while utilizing the extension cord 1104, including wearing the inductive track 1108 around his or her waist. Because power transfer is unaffected as long as any particular coil 248 in the array 1304 is generally adjacent to any point on the track 1108, the subject is generally free to move about on the mattress 1404 while still receiving a continuous power transfer. For example, the subject 704 may move longitudinally along the surface of the mattress 1404, as shown in FIG. 14A. By way of further example, the subject 704 may move across the surface of the mattress 1404 in a rolling motion as shown in FIG. 14B. It should be appreciated that the array 1304 of coils 248 is not limited to being placed in a mattress, but may instead be placed in other objects used by the subject 700. For instance, the array 1304 of coils 248 may be placed in a chair 1504, such as illustrated in FIG. 15. Additionally, in some implementations, the extension cord 1104 including the inductive track 1108 may be sewn into or otherwise incorporated in a shirt or vest 1604, as shown in FIGS. 16A-16B. Here, the shirt or vest 1604 may function as a convenient mechanism for maintaining the various coils in alignment for efficient power transfer.

In accordance with embodiments discussed herein, the first transformer 280, which is formed by the external coil 248 and the first extension cord coil 286, may be configured to be any shape or size, disposed in a location, or positioned in any orientation. When the distributed transformer 282 is associated with the external resonant network 120, the first transformer 280 is not constrained by considerations that limit the possible design configurations of the second transformer 284, which is formed by the second extension cord coil 290 and the internal coil 256. Because, in this configuration, the second transformer 284 transfers power across a skin second boundary 264, the coils of the second transformer 284 are specifically designed to avoid excess heating so as to prevent injury to the subject. The first transformer 280 does not operate under these constraints and so may include coils of size, shape, location, and so on. Thus, in accordance with various embodiments, the coils of the first transformer 280 are configured for a higher VA rating, larger coupling range between the windings, and/or higher temperature operation in comparison to the coils of the second transformer 284. By way of example, the circuit diagram of FIG. 6 shows coils of the first transformer 280 that have a greater number of windings as compared to the coils of the second transformer 284.

Generally, an extension cord that forms a distributed transformer 282 in accordance with the present disclosure may allow for a greater separation between the primary 248 of the first transformer 280 and the secondary 256 of the second transformer 284. Specifically, the extension cord can be used to separate the subject or patient from certain components of the external assembly 104, such as the controller 124. This aspect of the present disclosure may be advantageously used during the implantation process. In one respect, the extension cord allows the controller 124 to remain outside the sterile field. Here, the extension cord may be used during implantation to provide power as needed to the implant. Once the implantation is complete, the extension cord can be removed, sterilized, and used again for the next implantation.

Figure 17A:
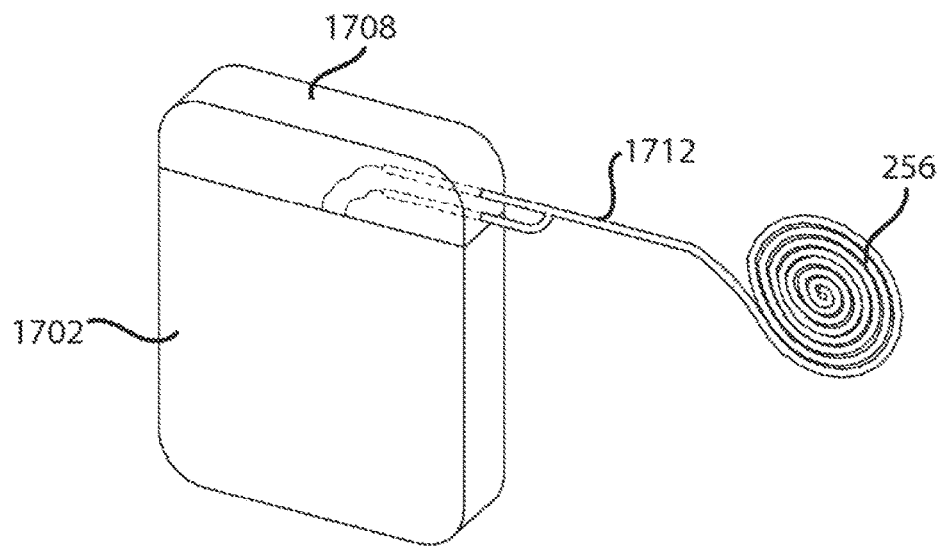
FIG. 17A is an illustration of various components of an internal assembly without a distributed transformer in place.

Distributed transformer implementations may include a cord or other attachment that couples to the internal resonant network 128. For example, a cord or other attachment may be used to form a distributed transformer that connects various components of the internal assembly 108. FIG. 17A is an illustration of various components of the internal assembly 108 without the cord in place. As shown in FIG. 17A, the internal assembly 108 may include an internal coil 256 that is electrically connected to a sealed package 1702. The sealed package 1702 may include various components that provide electrical power to an implanted medical device. For example, the sealed package 1702 may include various components that are more particularly illustrated in prior figures such as the regulator 156, rectifier 152, motor controller 136, and so on. A header 1708 portion of the sealed package 1702 may connect to a cable 1712 or wire that provides an electrical connection between the header 1702 and the internal coil 256. Without the use of a distributed transformer cord or other attachment, the header 1708 connects to the wire 1712 through a socket or other connection mechanism that must be specially sealed to protect the internal assembly and the subject within whom the internal assembly 108 is implanted. This seal can be costly to establish and maintain and can become a potential failure point of the system 100 as a whole.

Figure 17B:
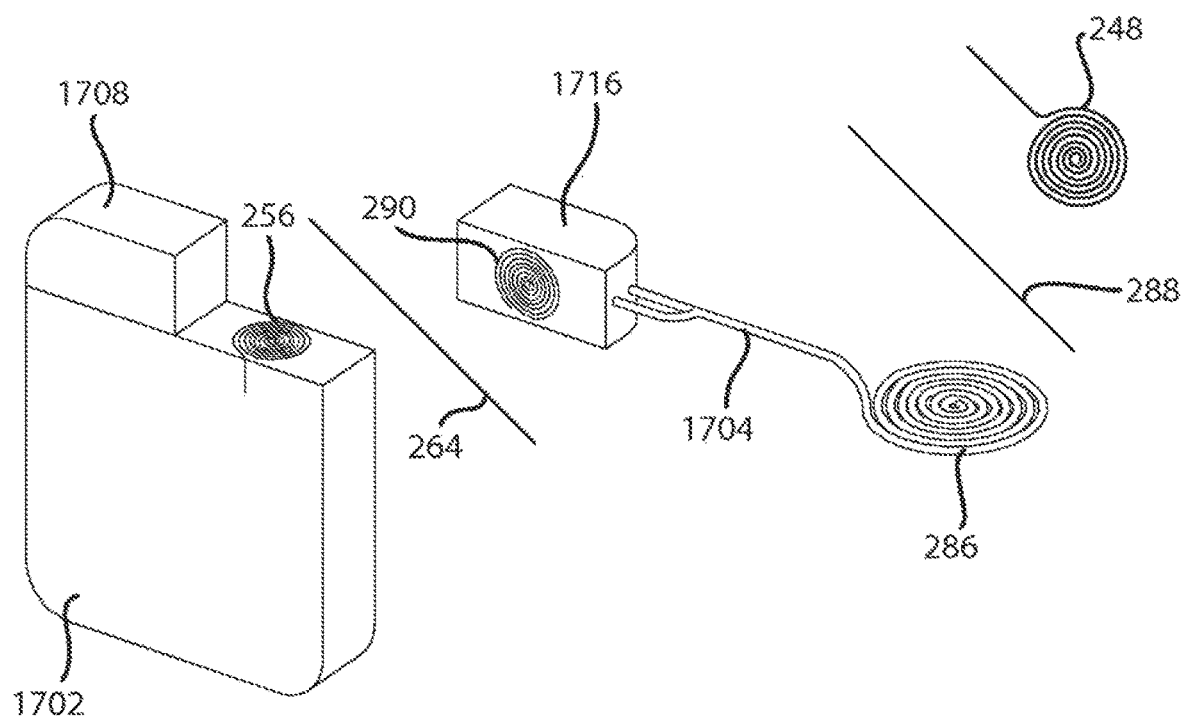
FIG. 17B is an illustration of various components of an internal assembly that includes a distributed transformer.

FIG. 17B is an illustration of various components of an internal assembly 108 that includes a distributed transformer cord or other attachment. As shown in FIG. 17B, the internal coil 256 may be included within the interior of the sealed package 1702. The internal coil 256 receives electrical power from an extension cord 1704 that, in turn, receives power from an external coil 248. As shown in FIG. 17B, the extension cord 1704 may include a first extension cord coil 286 that receives power across a first boundary 288 from the external coil 248. In this configuration, the first boundary 288 is the skin of the subject within whom the internal assembly is implanted. The extension cord 1704 may also include a second extension cord coil 290 that receives power across the length of the cord 1704 from the first extension cord coil 286. As shown in FIG. 17B, the second extension cord coil 290 may be included within a header attachment 1716. Once power is received at the second extension cord coil 290, power may transfer across the second boundary 264 to the internal coil 256. In this configuration, the second boundary 264 is a non-skin boundary that is disposed between the sealed package 1702 and the header 1708.

Using a distributed transformer cord 1704 in connection with the internal assembly 108 has many advantages. For example, using a distributed transformer cord 1704 enables a wireless transfer of power into the sealed package 1702. In the configuration of FIG. 17A, the current carrying wire 1712 extends from the header 1708 into the sealed package 1702. In contrast, in the configuration of FIG. 17B, power is wirelessly transferred from the header 1708 into the sealed package 1702 through the coupling between the second extension cord coil 290 and the internal coil 256. By making this power transfer wireless, using a distributed transformer cord 1704 avoids the need for special seals that would be otherwise be needed to enclose and protect the current-carrying wire's 1712 entry into the sealed package 1702. Thus, the non-skin boundary 264 between the header 1708 and the sealed package 1702 need not be enclosed or specially protected. Here, the power connection to the sealed package 1702 may be established by placing or otherwise orienting the header 1708 or header attachment 1716 adjacent to the sealed package 1702 such that the coils 256, 290 align. In some implementations, the header 1708 or header attachment 1716 may be held in place by a separate suture.

The invention claimed is:

1. A distributed transformer of a transcutaneous energy transmission device, the distributed transformer comprising:
    a power supply;
    a first transformer including a primary winding and a secondary winding, the primary winding adapted to receive power from the power supply, the first transformer configured to transfer power from the primary winding to the secondary winding across a first boundary that includes at least the skin of the subject;
    a second transformer including a primary winding and a secondary winding, the secondary winding electrically coupled to a medical device configured to be implanted within a subject, wherein the secondary winding of the second transformer and the medical device being housed within a sealed package, the second transformer configured to transfer power from the primary winding to the secondary winding across a second boundary;
    a cord that electrically connects the secondary winding of the first transformer to the primary winding of the second transformer; and
    a header attachment attached to the cord and configured to house the primary winding of the second transformer and to engage with the sealed package.

2. The distributed transformer of claim 1, wherein the medical device is a mechanical circulatory device.

3. The distributed transformer of claim 1, wherein the cord includes at least one capacitor connected between the secondary winding of the first transformer and the primary winding of the second transformer.

4. The distributed transformer of claim 1, wherein the first transformer is configured for a fixed implant location within the subject and wherein the second transformer is configured for any shape or size, any location, and any orientation or combination thereof.

5. The distributed transformer of claim 1, wherein the second boundary includes a portion of the medical device.

6. A distributed transformer device, the distributed transformer device comprising:
 a first transformer having a primary winding and a secondary winding, wherein the secondary winding is configured to receive power transferred from the primary winding of the first transformer across a first boundary that includes skin of a subject;
 a second transformer having a primary winding and a secondary winding, the secondary winding of the second transformer housed in a sealed package along with an implantable device, the second transformer configured to transfer power from the primary winding to the secondary winding across a second boundary;
 a cord that electrically connects the secondary winding of the first transformer to the primary winding of the second transformer; and
 a header attachment attached to the cord and configured to house the primary winding of the second transformer and to engage with the sealed package.

7. The distributed transformer device of claim 6, wherein the second boundary includes a portion of the sealed package.

8. The distributed transformer device of claim 6, wherein the secondary winding of the first transformer is configured for a fixed implant location within the subject and wherein the second transformer is configured for any implant location within the subject.

9. The distributed transformer device of claim 6, wherein the cord includes a capacitor connected between the secondary winding of the first transformer and the primary winding of the second transformer.

10. The distributed transformer device of claim 6, wherein the cord is configured to allow physical separation between a first location within the subject corresponding to the secondary winding of the first transformer and a second location within the subject corresponding to the primary winding of the second transformer.

11. The distributed transformer device of claim 6, further comprising a power supply coupled to the primary winding of the first transformer.

12. The distributed transformer device of claim 6, wherein the medical implantable device includes a ventricle-assist device.

13. The distributed transformer device of claim 6, wherein the medical implantable device includes an artificial heart.

* * * * *